US008641969B2

(12) United States Patent
Kitagawa et al.

(10) Patent No.: US 8,641,969 B2
(45) Date of Patent: Feb. 4, 2014

(54) SAMPLE TESTING APPARATUS WITH CONTROLED SAMPLE TRANSPORT MECHANISM CAPABLE OF TRANSPORT IN TWO OPPOSING DIRECTIONS

(75) Inventors: Nobuhiro Kitagawa, Akashi (JP); Hiroyuki Tanaka, Halstenbek (DE); Hiroo Tatsutani, Kobe (JP); Tomoyuki Asahara, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 12/727,586

(22) Filed: Mar. 19, 2010

(65) Prior Publication Data

US 2010/0248374 A1   Sep. 30, 2010

(30) Foreign Application Priority Data

Mar. 30, 2009   (JP) ................. 2009-083637

(51) Int. Cl.
*G01N 35/04* (2006.01)
*G01N 35/02* (2006.01)

(52) U.S. Cl.
USPC ............ 422/65; 422/63; 422/64; 422/67; 436/43; 436/47; 436/48; 436/50; 436/55

(58) Field of Classification Search
USPC ............ 422/63–65, 67; 435/286.1, 286.3, 435/287.1, 288.3; 436/43, 46–48, 50, 55, 436/66
See application file for complete search history.

(56) References Cited

U.S. PATENT DOCUMENTS

| | | | | |
|---|---|---|---|---|
| 3,985,507 A | * | 10/1976 | Litz et al. ..................... | 422/65 |
| 4,113,436 A | * | 9/1978 | Werder et al. ................ | 422/65 |
| 4,595,562 A | * | 6/1986 | Liston et al. .................. | 422/65 |
| 4,692,308 A | * | 9/1987 | Riley et al. ................... | 422/65 |
| 4,826,775 A | * | 5/1989 | Burns et al. .................. | 436/179 |
| 5,100,622 A | * | 3/1992 | Mimura et al. ............... | 422/67 |
| 5,207,986 A | * | 5/1993 | Kadota et al. ................ | 422/65 |
| 5,350,564 A | * | 9/1994 | Mazza et al. ................. | 422/63 |
| 5,582,796 A | * | 12/1996 | Carey et al. .................. | 422/65 |
| 5,623,415 A | * | 4/1997 | O'Bryan et al. ............. | 700/225 |
| 5,637,275 A | * | 6/1997 | Carey et al. .................. | 422/64 |
| 5,646,049 A | * | 7/1997 | Tayi ............................. | 436/518 |
| 5,902,549 A | * | 5/1999 | Mimura et al. ............... | 422/65 |
| 5,972,295 A | * | 10/1999 | Hanawa et al. .............. | 422/65 |
| 6,019,945 A | * | 2/2000 | Ohishi et al. ................. | 422/65 |
| 6,074,617 A | * | 6/2000 | DeYoung et al. ............ | 422/565 |
| 6,261,521 B1 | * | 7/2001 | Mimura et al. ............... | 422/67 |
| 6,319,718 B1 | * | 11/2001 | Matsubara et al. ........... | 436/47 |

(Continued)

FOREIGN PATENT DOCUMENTS

WO    2005/093433 A1    10/2005

*Primary Examiner* — Arlen Soderquist
(74) *Attorney, Agent, or Firm* — Sughrue Mion, PLLC

(57) ABSTRACT

The present invention is to present a sample testing apparatus comprising: a transport unit for transporting a sample container through a first position and a second position; a testing unit for performing a test on the sample in the sample container transported to the first position; a determination result obtainer for obtaining one of a first determination result indicating that a second test is required and a second determination result indicating that the second test is not required; and a transport controller for controlling the transport unit so as to transport the sample container back to the first position, if the first determination result has been obtained, wherein the sample container is not transported beyond the second position from the first position side before any one of the first and the second determination result has been obtained.

18 Claims, 21 Drawing Sheets

(56) References Cited

U.S. PATENT DOCUMENTS

| | | | |
|---|---|---|---|
| 6,522,976 B2 * | 2/2003 | Shiba et al. | 702/22 |
| 6,571,934 B1 * | 6/2003 | Thompson et al. | 198/619 |
| 6,579,717 B1 * | 6/2003 | Matsubara et al. | 436/50 |
| 6,588,625 B2 * | 7/2003 | Luoma et al. | 221/9 |
| 6,599,749 B1 * | 7/2003 | Kodama et al. | 436/47 |
| 6,635,488 B1 * | 10/2003 | Saito et al. | 436/43 |
| 6,752,960 B1 * | 6/2004 | Matsubara et al. | 422/63 |
| 6,827,902 B1 * | 12/2004 | Kuriyama et al. | 422/65 |
| 6,846,457 B1 * | 1/2005 | Tokiwa et al. | 422/67 |
| 7,028,831 B2 * | 4/2006 | Veiner | 198/619 |
| 7,101,715 B2 * | 9/2006 | Devlin et al. | 436/43 |
| 7,105,351 B2 * | 9/2006 | Matsubara et al. | 436/55 |
| 7,678,331 B2 * | 3/2010 | Shanafelter | 422/65 |
| 8,343,770 B2 * | 1/2013 | Hamada et al. | 436/48 |
| 2002/0064884 A1 * | 5/2002 | Devlin et al. | 436/174 |
| 2003/0089581 A1 * | 5/2003 | Thompson et al. | 198/619 |
| 2003/0129095 A1 * | 7/2003 | Farina et al. | 422/102 |
| 2003/0202905 A1 * | 10/2003 | Devlin et al. | 422/64 |
| 2005/0013737 A1 * | 1/2005 | Chow et al. | 422/63 |
| 2005/0194237 A1 * | 9/2005 | Veiner | 198/619 |
| 2005/0196320 A1 * | 9/2005 | Veiner et al. | 422/63 |
| 2005/0266570 A1 * | 12/2005 | Carey et al. | 436/43 |
| 2006/0216199 A1 | 9/2006 | Koike | |
| 2008/0020469 A1 * | 1/2008 | Barnes et al. | 436/46 |
| 2008/0050278 A1 * | 2/2008 | Farina et al. | 422/64 |
| 2009/0129990 A1 * | 5/2009 | Kokawa et al. | 422/104 |
| 2009/0263904 A1 * | 10/2009 | Clinton et al. | 436/48 |

* cited by examiner

| HOLDING POSITION | HOLDING FLAG | RETEST FLAG |
|---|---|---|
| 1 | 1 | 0 |
| 2 | 1 | 0 |
| 3 | 0 | |
| 4 | 1 | 0 |
| 5 | 1 | 0 |
| 6 | 1 | 1 |
| 7 | 0 | |
| 8 | 0 | |
| 9 | 0 | |
| 10 | 0 | |

F11  F12

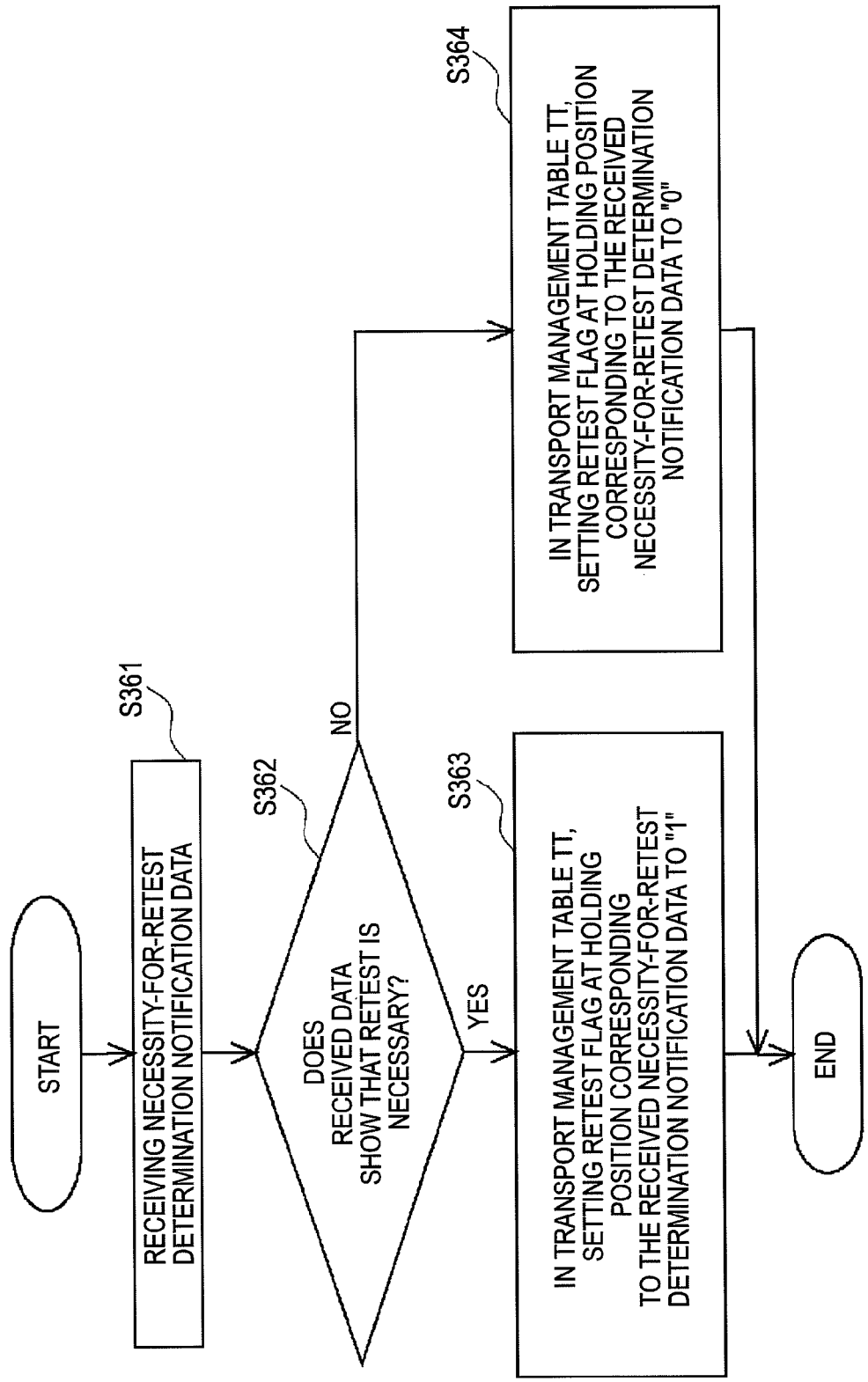

SAMPLE TESTING APPARATUS WITH CONTROLED SAMPLE TRANSPORT MECHANISM CAPABLE OF TRANSPORT IN TWO OPPOSING DIRECTIONS

FIELD OF THE INVENTION

The present invention relates to a sample testing apparatus and a sample testing method for transporting a sample and testing the transported sample.

BACKGROUND

Conventionally, there has been known a sample testing system which tests a sample such as blood or urine collected from a human subject such as a patient. In the sample testing system, the sample is automatically transported to a testing apparatus which carries out a first test (first-round test) on the sample. When the first-round test result of the sample departs from a normal range, the sample is automatically transported to the testing apparatus which carries out a second test (retest) on the sample.

In US Patent Publication No. 2006-216199, a system is disclosed which includes a first blood analysis apparatus for carrying out a primary analysis, a second blood analysis apparatus for carrying out a secondary analysis, and a transport apparatus which has a function to transport a rack accommodating sample containers to each sample supply position of the first blood analysis apparatus and the second blood analysis apparatus. In the system, the primary analysis by the first blood analysis apparatus is carried out on all the samples, and the secondary analysis by the second blood analysis apparatus is carried out only on the sample for which it is determined that a detailed analysis needs to be carried out based on the primary analysis result.

In WO 2005/093433, a sample transport module is disclosed which is configured to be used with each of plural sample processing instruments of a multi-instrument clinical work cell. The sample transport module includes a sample aspiration station for supporting a sample container rack on a position to which an aspiration probe of the sample processing instrument approaches, and a housing for partitioning an buffer for supporting the plural sample container racks on a position from which the sample container rack is removed from the sample transport module. The sample transport module transports a received sample container rack to the sample aspiration station, and delivers the sample container rack to the buffer after the sample aspiration from the sample container in the sample container rack. In addition, the sample transport module can return the sample container rack, which has been delivered to the buffer, to the sample aspiration station for reflex or repeat testing, when a first test result indicates that a second aspiration of a specific sample needs to be carried out or when the first test result is obviously in error. In the sample transport module, an X/Y movable truck is provided to press the sample container rack into the buffer. The X/Y movable truck can take out the final sample container rack in a waiting line in order to carry out the repeat testing or the reflex testing.

However, in the system disclosed in US Patent Publication No. 2006-216199, there is a problem that the system is complicated because the second blood analysis apparatus for the secondary analysis is necessary.

In the sample transport module described in WO 2005/093433, when it takes a longer time than expected until the reflex testing or the repeat testing is determined to be necessary, the sample container rack holding the sample which requires the reflex testing or the repeat testing may be pushed into the buffer and another sample container rack may exist behind the sample container rack at the time when the determination result is obtained. A technique for automatically returning the sample container rack to the sample aspiration station is not disclosed in WO 2005/093433.

SUMMARY

The scope of the present invention is defined solely by the appended claims, and is not affected to any degree by the statements within this summary.

A first aspect of the present invention is a sample testing apparatus comprising: a transport unit for transporting a sample container containing a sample through a first position and a second position; a testing unit for aspirating the sample from the sample container transported to the first position by the transport unit and for performing a test on the aspirated sample; a determination result obtainer for obtaining one of a first determination result indicating that a second test is required for the sample and a second determination result indicating that the second test is not required for the sample, based on a test result of a first test on the sample; and a transport controller for controlling the transport unit so as to transport the sample container back to the first position, the sample container containing the sample on which the first test has been performed, if the determination result obtainer has obtained the first determination result on the sample, wherein the sample container is not transported beyond the second position from the first position side before the determination result obtainer has obtained any one of the first and the second determination result on the sample.

A second aspect of the present invention is a sample testing apparatus comprising: a transport unit for transporting a sample container containing a sample through a first position and a second position; a testing unit for aspirating the sample from the sample container transported to the first position by the transport unit and performing a test on the aspirated sample; a determination result obtainer for obtaining one of a first determination result indicating that a second test is required for the sample and a second determination result indicating that the second test is not required for the sample, based on a test result of a first test on the sample; and a transport controller for controlling the transport unit so as to keep the sample container waiting at the second position, the sample container containing the sample on which the first test has been performed, until the determination result obtainer has obtained any one of the first and the second determination result on the sample, if the determination result obtainer has not obtained any one of the first and the second determination result on the sample when the sample container has reached the second position, and for controlling the transport unit so as to transport the sample container back to the first position if the determination result obtainer has obtained the first determination result on the sample.

A third aspect of the present invention is a sample testing method comprising steps of: (a) aspirating a sample from a sample container transported to a first position by a transport unit and performing a first test on the aspirated sample; (b) obtaining one of a first determination result indicating that a second test is required for the sample and a second determination result indicating that the second test is required for the sample, based on a test result of the first test on the sample; (c) transporting the sample container back to the first position by the transport unit if the first determination result on the sample has been obtained in the step (b); and (d) aspirating the sample from the sample container transported to the first position by the transport unit and performing the second test on the aspirated sample, if the first determination result on the sample has been obtained in the step (b), wherein the sample container is not transported beyond the second position from the first position side before any one of the first and the second determination result on the sample has been obtained in the step (b).

BRIEF DESCRIPTION OF THE DRAWINGS

FIG. 15 is a diagram schematically illustrating the structure of a transport management table;

FIG. 17 is a flowchart illustrating the flow of a necessity-for-retest determination notification receiving process carried out by an information processing unit according to an embodiment;

DETAILED DESCRIPTION OF THE EMBODIMENT

Hereinafter, an exemplary embodiment of the invention will be described with reference to the drawings.

This embodiment relates to a sample testing system which is provided with a testing apparatus and a transport apparatus which transports a sample rack accommodating a plurality of samples. In the sample testing system, the testing apparatus carries out a first test (first-round test) on a sample which is transported by the transport apparatus, and then transports the sample rack in a predetermined first transport direction so as not to exceed a predetermined position of the transport apparatus until the determination of necessity for a second test (retest) is carried out. When it is determined that the retest is necessary, the sample testing system transports the sample in a second transport direction opposite to the first transport direction in order to perform the retest of the sample by the testing apparatus.

[Configuration of Sample Testing System]

Figure 1:
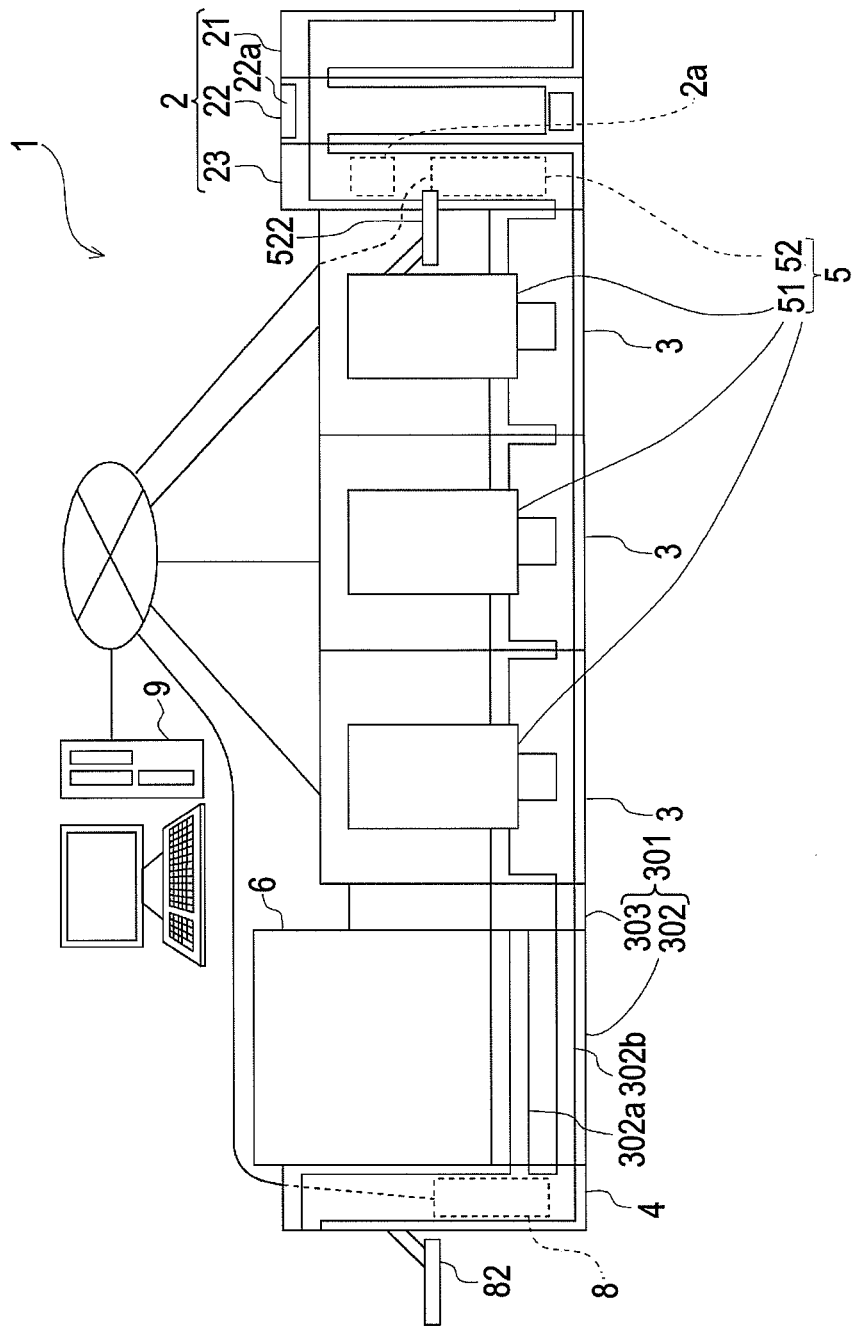
FIG. 1 is a schematic plan view illustrating the entire configuration of a sample testing system according to an embodiment.

FIG. 1 is a schematic plan view illustrating the entire configuration of a sample testing system according to this embodiment. As shown in FIG. 1, the sample testing system 1 is provided with a sample putting apparatus 2, a sample transport apparatus 3, a sample transport apparatus 301, a sample accommodating apparatus 4, a sample testing apparatus 5, a smear slide preparing apparatus 6, and a system control apparatus 8. In addition, the sample testing system 1 according to this embodiment is connected to a testing information management apparatus 9 via a communication network so as to perform communication therewith.

<Configuration of Sample Putting Apparatus 2>

The sample putting apparatus 2 is provided with a sample putting unit 21, a bar-code reading unit 22, and a sample delivery unit 23. The bar-code reading unit 22 is disposed between the sample putting unit 21 and the sample delivery unit 23. The sample putting unit 21 is configured to transport the sample loaded in the sample putting unit 21 to the sample delivery unit 23 via the bar-code reading unit 22. The sample putting unit 21 and the sample delivery unit 23 are configured to place a sample rack which accommodates a plurality of the sample containers to be described later. The sample rack placed in the sample putting unit 21 is sequentially fed to the bar-code reading unit 22. The bar-code reading unit 22 reads a rack ID from the bar-code written on a bar-code label patched on the sample rack. A sample ID is read from the bar-code written on the bar-code label patched on the sample container.

Figure 2:
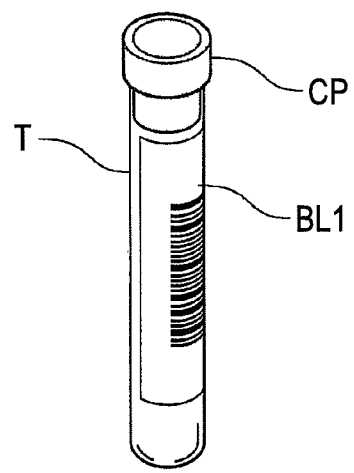
FIG. 2 is a perspective view illustrating an appearance of a sample container.
Figure 3:
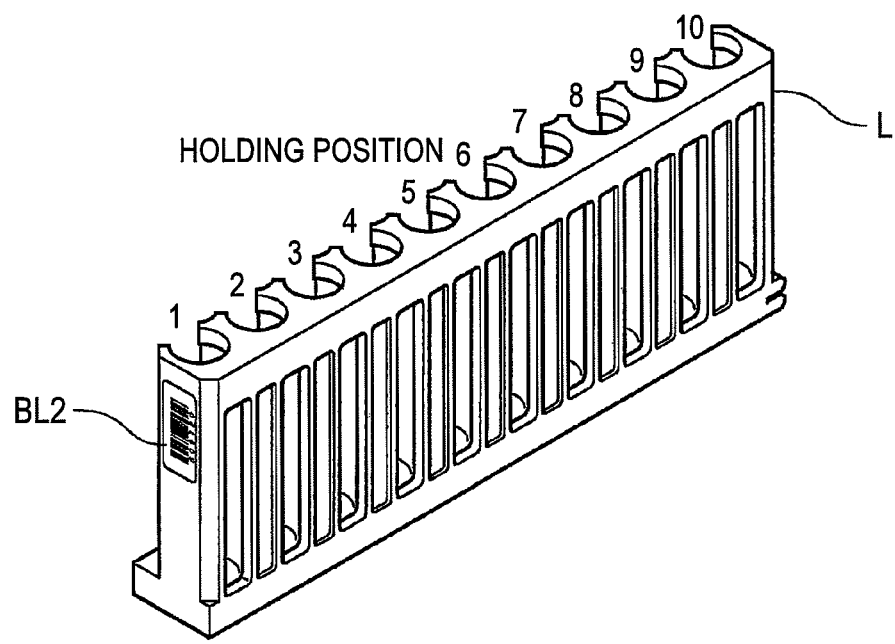
FIG. 3 is a perspective view illustrating an appearance of a sample rack.

FIG. 2 is a perspective view illustrating an appearance of the sample container. FIG. 3 is a perspective view illustrating an appearance of the sample rack. As shown in FIG. 2, the sample container T is formed in a tubular shape, and the upper end is opened. A blood sample gathered from a patient is accommodated in the sample container, and the opening on the upper end is sealed by a cap section CP. The sample container T is made of a transparent glass or a transparent synthetic resin, so that the blood sample therein is visible. In addition, the side surface of the sample container T is patched with a bar-code label BL1. A bar-code indicating the sample ID is printed on the bar-code label BL1. A sample rack L can arrange and hold 10 sample containers T. Each sample container T is held in a vertical state (upright state) on the sample rack L. In addition, a bar-code label BL2 is patched on the side surface of the sample rack L. A bar-code indicating the rack ID is printed on the bar-code label BL2.

The above-mentioned bar-code reading unit 22 is provided with a bar-code reader 22a which includes a rotating apparatus. The bar-code reading unit is configured to read the sample bar-code of the sample container T, while the plural sample containers T held on the sample rack L are rotated in a substantially horizontal direction by the rotating apparatus in a state of being accommodated in the sample rack L. Therefore, even when the bar-code label BL1 of the sample container T is positioned on the opposite side of the bar-code reader 22a, the bar-code label BL1 can face the bar-code reader 22a by rotating the sample container T, so that the sample bar-code can be read by the bar-code reader 22a.

In addition, the sample putting apparatus 2 is provided with a controller 2a which is constituted by a CPU and a memory. The sample putting apparatus 2 can control operation mechanisms of the sample putting unit 21, the bar-code reading unit 22, and the sample delivery unit 23 by using the controller 2a. The controller 2a of the sample putting apparatus 2 is connected to the system control apparatus 8 via a LAN so as to perform communication therewith. The controller transmits the rack ID and the sample ID, which are read as described above, to the system control apparatus 8. In addition, the sample rack of which the bar-code is read is configured to be transported to the sample delivery unit 23 and then transported from the sample delivery unit 23 to the sample transport apparatus 3.

<Configuration of Sample Transport Apparatus 3>

Next, the configuration of the sample transport apparatus 3 will be described. As shown in FIG. 1, the sample testing system 1 includes three sample transport apparatuses 3. The sample transport apparatuses 3, 3 and 3 are each disposed in front of three measuring units 51, 51 and 51 of the sample testing apparatus 5. Neighboring sample transport apparatuses 3 and 3 are connected to each other so as to send and receive the sample rack L to and from each other. The rightmost sample transport apparatus 3 is connected to the above-described sample putting apparatus 2 so as to feed the sample rack L unloaded from the sample putting apparatus 2 thereto. The leftmost sample transport apparatus 3 is connected to the sample transport apparatus 301 so as to unload the sample rack L to the sample transport apparatus 301.

Figure 4:
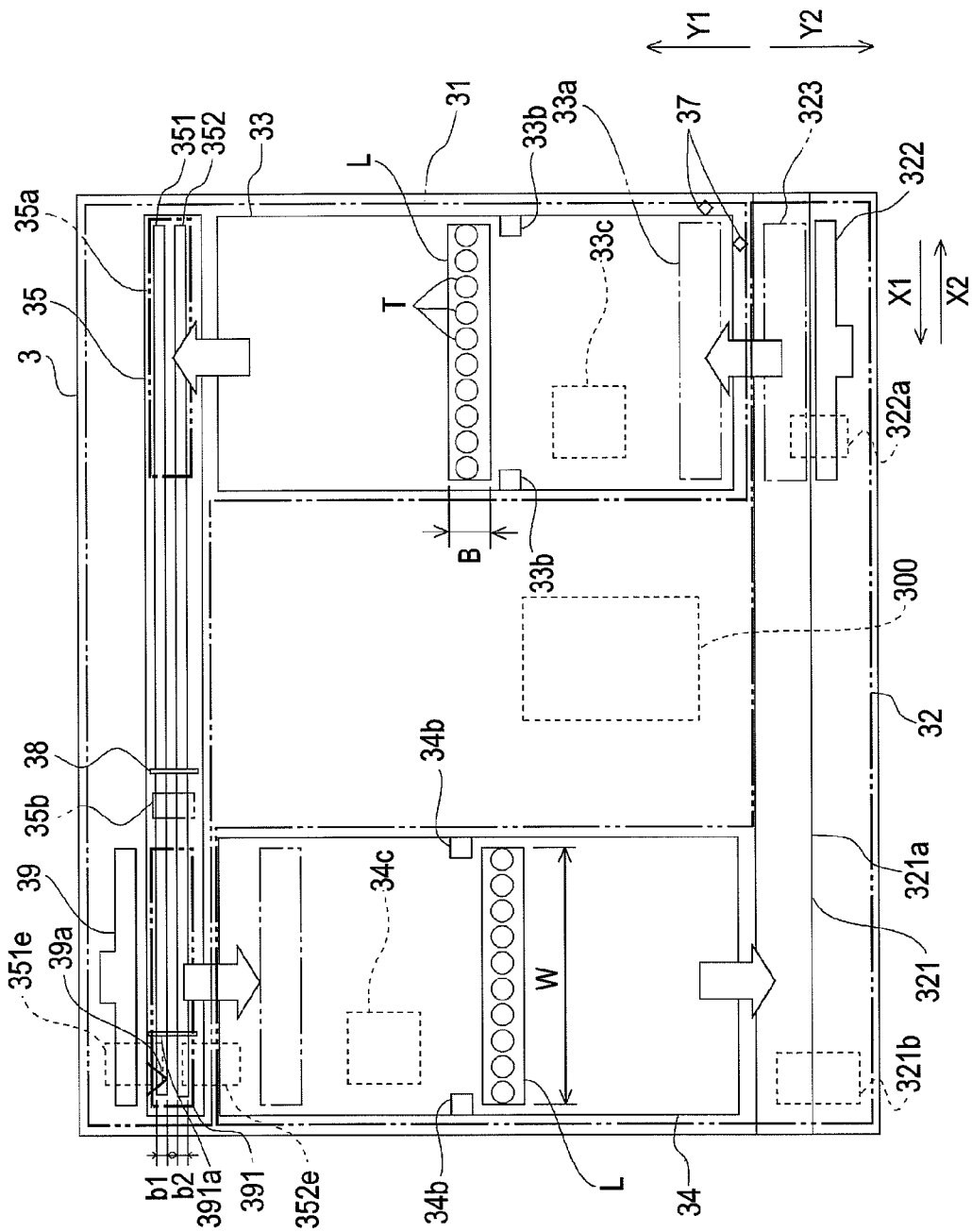
FIG. 4 is a plane view illustrating the configuration of a sample transport apparatus according to an embodiment.

FIG. 4 is a plan view illustrating the configuration of the sample transport apparatus 3. As shown in FIG. 4, the sample transport apparatus 3 is provided with a first transport mechanism 31 for supplying the sample to the measuring unit 51 of the sample testing apparatus 5, a second transport mechanism 32 for transporting the sample to the sample transport apparatus 3 (or the sample transport apparatus 310) which is disposed on the downstream side, and a control section 300 for controlling the second transport mechanism. The first transport mechanism 31 is provided with a before-analysis rack holding section 33 which can temporarily hold the plural sample racks L holding the sample containers T which contain the samples not yet analyzed, a rack transport section 35 which linearly moves the sample rack L parallel in an arrow direction X1 (left direction) and an arrow direction X2 (right direction) in the drawing, a rack sensor 37 which detects the existence of the sample rack L, a sample container sensor 38 which detects the existence of the sample container T, and a rack delivery section 39 which delivers the sample rack L to the second transport mechanism 32.

The before-analysis rack holding section 33 has a quadrangular shape when viewed from above, and its width is slightly larger than the width of the sample rack L. The before-analysis rack holding section 33 is formed to be lower by one stage than the surrounding surface, and on an upper face thereof, the before-analysis sample racks L are placed. The before-analysis rack holding section 33 is connected to the second transport mechanism 32, and the sample rack L is sent from the second transport mechanism 32 by a rack delivery section 322 of the second transport mechanism 32 to be described later. The rack sensor 37 is installed near the before-analysis rack holding section 33, and a rack detection position 33a at which the sample rack L is detected by the rack sensor 37 is provided on the before-analysis rack holding section 33. The sample rack L sent from the second transport mechanism 32 is positioned at the rack detection position 33a, and thereby the sample rack L is detected by the rack sensor 37. In addition, rack sending sections 33b are provided in both faces of the before-analysis rack holding section 33 so as to protrude inward. When the sample rack L is detected by the rack sensor 37, the rack sending sections 33b protrude so as to be engaged with the sample rack L. In this state, the rack sending sections 33b are moved in the direction Y1 (backward, a direction so as to be closer to the rack transport section 35) and thus the sample rack L is moved in the direction Y1. Therefore, the sample rack L on the before-analysis rack holding section 33 is transported in the direction Y1 up to a sending position 35a on the right end of the rack transport section 35. The rack sending sections 33b are configured to be driven by a stepping motor 33c provided below the before-analysis rack holding section 33.

As shown in FIG. 4, the rack transport section 35 can move the sample rack L, which is moved to the sending position 35a by the before-analysis rack holding section 33, in the X1 direction. On the path of the transport of the sample rack L by the rack transport section 35, there is a sample supply position 35b for supplying the sample to the measuring unit 51 of the sample testing apparatus 5. The rack transport section 35 is configured to transport the sample rack L positioned at the sending position 35a so that the sample is transported to the sample supply position 35b. When the sample is transported to the sample supply position 35b by the rack transport section 35, a hand section of the measuring unit 51 of the sample testing apparatus 5 to be described later grasps the sample container T of the sample and takes out the sample container T from the sample rack L, and the sample container T is taken into the measuring unit 51 and the sample is aspirated, and thus the sample is supplied to the measuring unit 51. After transporting the sample container to the sample supply position 35b, the rack transport section stands by to transport the sample rack L while the supplying of the sample is completed and the sample container T is returned to the sample rack L.

Figure 5:
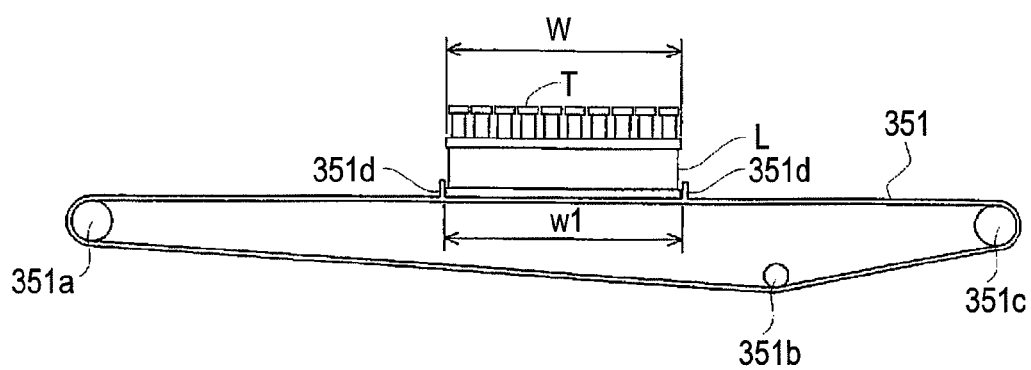
FIG. 5 is a front view illustrating the configuration of a first belt provided at a first transport mechanism.
Figure 6:
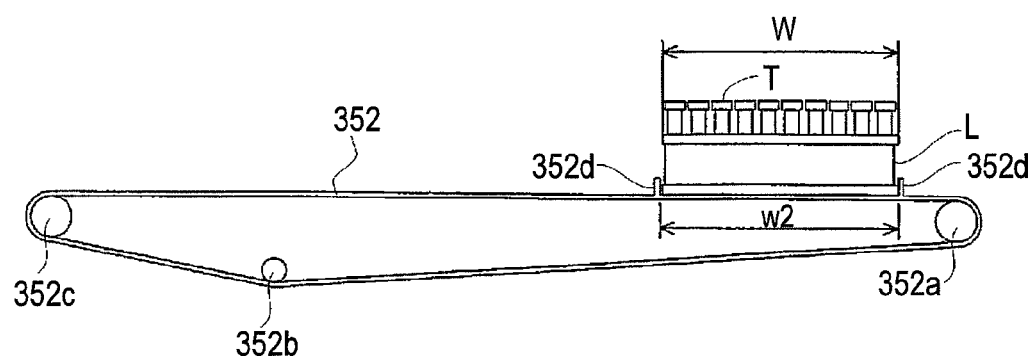
FIG. 6 is a front view illustrating the configuration of a second belt provided at the first transport mechanism.

In addition, the rack transport section 35 has two independently operable belts, that is, a first belt 351 and a second belt 352. Widths b1 and b2 in a direction of the arrow Y1 of the first belt 351 and the second belt 352 are respectively equal to or smaller than half of a width B in the direction of the arrow Y1 of the sample rack L. The first belt 351 and the second belt 352 are disposed in parallel so as not to protrude from the width B of the sample rack L when the rack transport section 35 transports the sample rack L. FIG. 5 is a front view illustrating the configuration of the first belt 351 and FIG. 6 is a front view illustrating the configuration of the second belt 352. As shown in FIGS. 5 and 6, the first belt 351 and the second belt 352 are annularly formed respectively. The first belt 351 is disposed so as to surround rollers 351a to 351c and the second belt 352 is disposed so as to surround rollers 352a to 352c. In the outer peripheral section of the first belt 351, two protrusions 351d are provided so as to have an inner width w1 slightly larger (for example, 1 mm) than a width W in the X1 direction of the sample rack L, and similarly, in the outer peripheral section of the second belt 352, two protrusions 352d are provided so as to have the substantially same inner width w2 as the inner width w1. The first belt 351 is configured so that the sample rack L held inside the two protrusions 351d is moved in the direction of the arrow X1 by being moved along the outer peripheries of the rollers 351a to 351c by a stepping motor 351e. The second belt 352 is configured so that the sample rack L held inside the two protrusions 352d is moved in the direction of the arrow X2 by being moved along the outer peripheries of the rollers 352a to 352c by a stepping motor 352e. In addition, the first belt 351 and the second belt 352 are configured so as to move the sample rack L independently of each other.

Each of the rack sensor 37 and the sample container sensor 38 is a contact sensor and has a contact piece in a curtain shape, a light-emitting element for emitting light and a light-receiving element (not shown). Each of the rack sensor 37 and the sample container sensor is configured so that the contact piece is bent when brought into contact with a substance to be detected which is a detection object and the light emitted from the light-emitting element is thus reflected by the contact piece and enters the light-receiving element. Accordingly, while the sample container T which is a detection object accommodated in the sample rack L passes under the sample container sensor 38, the contact piece is bent by the sample container T and the sample container T can be detected.

With the above-mentioned configuration of the rack transport section 35, the sample rack L is transported to a leftmost position 391 (hereinafter, referred to as "after-analysis rack delivery position") of the rack transport section 35. A contact rack sensor 391a is provided near the after-analysis rack delivery position 391. When the sample rack L transported by the rack transport section 35 reaches the rack delivery position 391, the sample rack L is detected by the rack sensor 391a. The output signals of the above-mentioned rack sensors 37 and 391a and the sample container sensor 38 are given to an information processing unit 52 of the sample testing apparatus 5.

The rack delivery section 39 is disposed so as to be opposed to an after-analysis rack holding section 34 to be described later with the rack transport section 35 interposed therebetween. The rack delivery section 39 is configured to be horizontally moved in a straight line in the direction of the arrow Y2 by a driving force of a stepping motor 39a. Accordingly, when the sample rack L is transported to the after-analysis rack delivery position 391 between the after-analysis rack holding section 34 and the rack delivery section 39, by moving the rack delivery section 39 toward the after-analysis rack holding section 34, the sample rack L can be pushed so as to be moved to the inside of the after-analysis rack holding section 34. In this manner, the sample rack L in which the analysis has been completed is delivered from the first transport mechanism 31 to the second transport mechanism 32.

The second transport mechanism 32 is provided with a rack transport section 321, the rack delivery section 322, and the after-analysis holding section 34. The rack transport section 321 extends in the direction of the arrow X1 in the drawing and can horizontally move the sample rack L in a straight line in the direction of the arrow X1. The rack transport section 321 has an annular belt 321a and a stepping motor 321b and is configured so as to rotate the belt 321a in the direction of the arrow X1 by a driving force of the stepping motor 321b. Accordingly, the sample rack L placed on the belt 321a can be moved in the X1 direction. In addition, the rack delivery section 322 is disposed in front of the before-analysis rack holding section 33 so as to be opposed to the before-analysis rack holding section 33 with the rack transport section 321 interposed therebetween. The rack delivery section 322 is configured to be horizontally moved in a straight line in the direction of the arrow Y1 by a driving force of a stepping motor 322a. Accordingly, when the sample rack L is transported to a position 323 (hereinafter, referred to as "before-analysis rack delivery position") between the before-analysis rack holding section 33 and the rack delivery section 322, by moving the rack delivery section 322 toward the before-analysis rack holding section 33, the sample rack L can be pushed so as to be moved to the rack detection position 33a in the before-analysis rack holding section 33. In addition, the rack transport section 321 is not driven in the direction X2 opposite to the direction X1. Therefore, by configuring the rack transport section 321 to be driven only in one direction (the direction X1), the complexity of the configuration of the sample transport apparatus 3 and the increase in size of the sample transport apparatus 3 is suppressed.

The after-analysis rack holding section 34 has a quadrangular shape when viewed from above, and its width is slightly larger than the width of the sample rack L. The after-analysis rack holding section 34 is formed to be lower by one stage than the surrounding surface, and on an upper face thereof, the sample racks L in which the analysis has been completed are placed. The after-analysis rack holding section 34 is connected to the rack transport section 35, and as described above, the sample rack L is sent from the rack transport section 35 by the rack delivery section 39. Rack sending sections 34b are provided in both faces of the after-analysis rack holding section 34 so as to protrude inward. When the sample rack L is loaded by the rack delivery section 39, the rack sending sections 34b protrude so as to be engaged with the sample rack L. In this state, the rack sending sections are moved in the direction Y2 (forward, a direction so as to be closer to the rack transport section 321) and thus the sample rack L is moved in the direction Y2. The rack sending sections 34b are configured to be driven by a stepping motor 34c provided below the after-analysis rack holding section 34.

The second transport mechanism 32 having the above-described configuration is controlled by the control section 300. On the other hand, the first transport mechanism 31 is controlled by the information processing unit 52 of the sample testing apparatus 5 to be described later. The control section 300 is composed of a CPU, a ROM, a RAM and the like (not shown) and a control program of the second transport mechanism 32, which is stored in the ROM, can be executed by the CPU. The control section 300 includes an Ethernet (registered trade name) interface and is connected to the information processing unit 52 and the system control apparatus 8 via a LAN so as to communicate therewith.

Due to the above-described configuration, the sample transport apparatus 3 transports the sample rack L, which is transported from the sample putting apparatus 2, to the before-analysis rack delivery position 323 by using the second transport mechanism 32, moves the sample rack to the before-analysis rack holding section 33 of the first transport mechanism by using the rack delivery section 322, delivers the sample rack L from the before-analysis rack holding section 33 to the rack transport section 35, and also transports the sample rack by using the rack transport section 35, and thus the sample can be supplied to the measuring unit 51 of the sample testing apparatus 5. In addition, the sample rack L, which accommodates the sample for which the aspiration has been completed, is transported in the direction X1 by the rack transport section 35, and moved to the after-analysis rack delivery position 391. As to be described later, in a case where it is determined that the sample, which is held on the sample rack L, requires the retest before reaching the after-analysis rack delivery position 391, the delivery direction of the rack transport section 35 is immediately switched from the direction X1 to the direction X2 in order to carry out the retest by the sample testing apparatus 5, and the sample moves to the sample supply position 35b. In addition, in a case where at least one of the samples, which are held on the sample rack L, is not determined as requiring the retest or not when the sample rack L reaches the after-analysis rack delivery position 391, the sample rack L stands by at the after-analysis rack delivery position 391 until it is determined whether or not the retest is required. When it is determined that the retest is required, the sample rack L is transported in the direction X2 by the rack transport section 35 in order to carry out the retest of the sample. On the other hand, when it is determined that the retest is not required or when a time-out occurs, the sample rack L at the after-analysis rack delivery position 391 is delivered to the after-analysis rack holding section 34 by the rack delivery section 39. The sample rack L held on the after-analysis rack holding section 34 is moved to the rack transport section 321 of the second transport mechanism 32 and is unloaded to the following apparatus (sample transport apparatus 3 or 301) by the rack transport section 321. When the sample rack L, which accommodates the samples to be processed by the measuring unit 51 or the smear slide preparing apparatus 6 on the downstream side of the transport or the samples in which the analysis has been completed, is received by the sample transport apparatus 3 from the preceding apparatus, the sample rack L is transported in the direction of the arrow X by the rack transport section 321 of the second transport mechanism 32 and is unloaded to the following sample transport apparatus 3.

<Configuration of Sample Transport Apparatus 301>

As shown in FIG. 1, the sample transport apparatus 301 is disposed in front of the smear slide preparing apparatus 6. The right end of the sample transport apparatus 301 is connected to the sample transport apparatus 3 positioned on the downmost-stream side of the transport (left side in the drawing) among the three sample transport apparatuses 3, 3 and 3. The left end of the sample transport apparatus 301 is connected to the sample accommodating apparatus 4.

The sample transport apparatus 301 includes a conveyor 302 and a rack slider 303. The conveyor 302 is provided with two rack transport paths 302a and 302b extending in a horizontal direction. The rack transport path 302a which is closer to the smear slide preparing apparatus 6 is a measuring line for transporting the sample rack L accommodating the sample to be supplied to the smear slide preparing apparatus 6. On the other hand, the rack transport path 302b which is separated from the smear slide preparing apparatus 6 is a skip line for transporting the sample rack L not accommodating the sample to be supplied to the smear slide preparing apparatus 6. In addition, the conveyor 302 includes a CPU, a memory and a control section (not shown) for controlling the operating mechanisms.

The rack slider 303 is disposed on the right side of the conveyor 302, and sorts and puts the sample racks L to the measurement line 302a and the skip line 302b of the conveyor 302.

<Configuration of Sample Accommodating Apparatus 4>

The sample accommodating apparatus 4 is configured so that the plural sample racks L can be placed. The sample accommodating apparatus 4 receives from the sample transport apparatus 301 the sample rack L in which the analysis or the smear slide preparation has been completed, and accommodates the sample rack L.

<Configuration of Sample Testing Apparatus 5>

The sample testing apparatus 5, which is used as an optical flow cytometry type multiple blood cell analyzing apparatus, obtains the fluorescent intensity, the side-scattered light intensity and the like of blood cells included in a blood sample, classifies the blood cells included in the sample based on the above intensities, and counts the number of blood cells for each type. Moreover, the blood cell analyzing apparatus 5 creates a scattergram in which the classified blood cells are color-coded for each type, and displays the scattergram. The sample testing apparatus 5 includes the measuring units 51 for measuring a blood sample and the information processing unit 52 for processing measuring data output from the measuring unit 51 and displaying analysis results of the blood sample.

As shown in FIG. 1, the sample testing apparatus 5 includes the three measuring units 51, 51 and 51 and the one information processing unit 52. The information processing unit 52 is connected to the two measuring units 51 and 51 and the three sample transport apparatuses 3, 3 and 3 so as to communicate therewith and can control the operations of the three measuring units 51, 51 and 51 and the three first transport mechanisms 31, 31 and 31.

Figure 7:
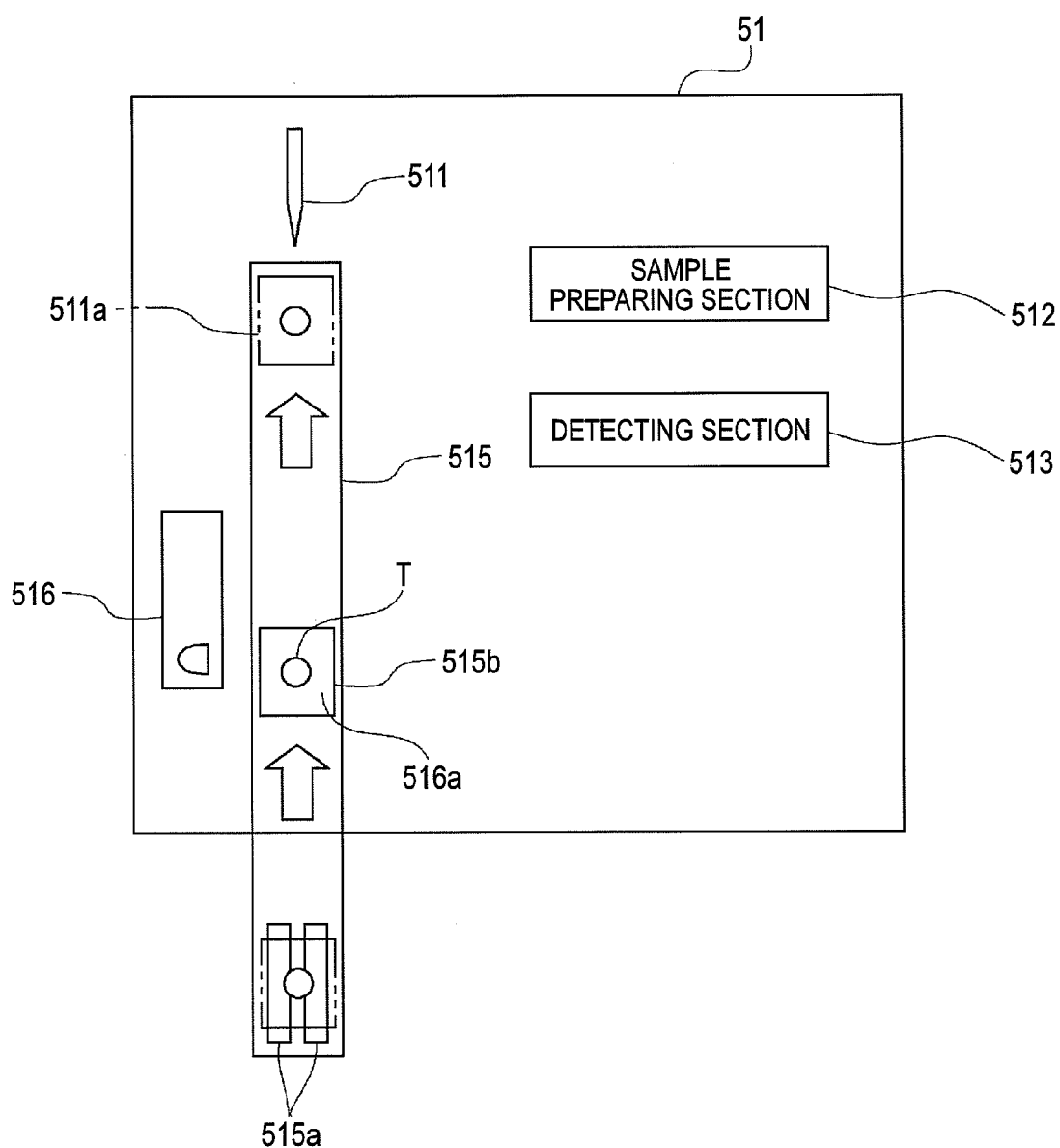
FIG. 7 is a block diagram illustrating the configuration of a measuring unit of a sample testing apparatus according to an embodiment.

In addition, the three measuring units 51, 51 and 51 have the same configuration. FIG. 7 is a block diagram illustrating the configuration of the measuring unit 51. As shown in FIG. 7, the measuring unit 51 includes a sample aspirating section 511 for aspirating blood which is a sample from the sample container (blood collection tube) T, a sample preparing section 512 for preparing a measurement sample which is used in the measurement from the blood aspirated by the sample aspirating section 511 and a detecting section 513 for detecting a blood cell from the measurement sample prepared by the sample preparing section 512. In addition, the measuring unit 51 further has a taking port (not shown) for taking the sample container T accommodated in the sample rack L transported by the rack transport section 35 of the sample transport apparatus 3 into the measuring unit 51, and a sample container transport section 515 for taking the sample container T from the sample rack L into the measuring unit 51 and transporting the sample container T to an aspiration position where the aspiration is performed by the sample aspirating section 511.

An aspiration tube (not shown) is provided at the tip end of the sample aspirating section 511. In addition, the sample aspirating section 511 is configured to be vertically movable, and moved downward, so that the aspiration tube penetrates into the cap section CP of the sample container T transported to the aspiration position so as to aspirate the blood in the sample container.

The detecting section 513 can detect red blood cells (RBC) and platelets (PLT) by using a sheath flow DC detection method. In detecting RBCs and PLTs by using the sheath flow DC detection method, a measurement sample in which a sample and a diluent are mixed is measured, and measuring data obtained in this manner is analyzed by the information processing unit 52 so as to measure the RBCs and PLTs. In addition, the detecting section 513 is configured to detect hemoglobin (HGB) by using a SLS-hemoglobin method and detect white blood cells (WBC), neutrophils (NEUT), lymphocytes (LYMPH), eosinophils (EO), basophil (BASO) and monocytes (MONO) by using a flow cytometry method using semiconductor lasers. In addition, the detecting section 513 can measure the platelets (PLT-O) by using an optical flow cytometry method in addition to the PLT measurement by the above-mentioned sheath flow DC detection method.

The above-mentioned WBC, RBC, PLT, and HGB are included by a measuring item referred to as a CBC item. The WBC, RBC, PLT, HGB, NEUT, LYMPH, EO, BASO, and MONO are included by a measuring item referred to as a CBC+DIFF item.

The sample container transport section 515 includes a hand section 515a capable of grasping the sample container T. The hand section 515a includes a pair of grasping members opposed to each other and can allow the grasping members to be closer to each other or farther from each other. The sample container T can be held by allowing the grasping members with the sample container T interposed therebetween to be closer to each other. In addition, the sample container transport section 515 can move the hand section 515a in a vertical direction and in a front-back direction (Y1 and Y2 directions) and can oscillate the hand section 515a. Accordingly, by holding the sample container T accommodated in the sample rack L and positioned at the sample supply position 35b with the hand section 515a and moving the hand section 515a upward in this state, the sample container T is pulled out of the sample rack L, and by oscillating the hand section 515a, the sample in the sample container T can be stirred.

In addition, the sample container transport section 515 includes a sample container setting section 515b having a hole to which the sample container T can be inserted. The sample container T grasped by the above-described hand section 515a is moved after the completion of stirring and the grasped sample container T is inserted into the hole of the sample container setting section 515b. Then, by allowing the grasping members to be separated from each other, the sample container T is released from the hand section 515a and the sample container T is set in the sample container setting section 515b. The sample container setting section 515b can be horizontally moved in the Y1 and Y2 directions by the power of a stepping motor (not shown). A bar-code reading section 516 is provided in the measuring unit 51. The sample container setting section 515b can be moved to a bar-code reading position 516a near the bar-code reading section 516 and an aspiration position 511a where the aspiration is performed by the sample aspirating section 511. When the sample container setting section 515b is moved to the bar-code reading position 516a, the set sample container T is horizontally rotated by a rotation mechanism (not shown) and the sample bar-code is read by the bar-code reading section 516. Accordingly, even when the bar-code label BL1 of the sample container T is positioned on the opposite side with respect to the bar-code reading section 516, the bar-code label BL1 can face the bar-code reading section 516 by rotating the sample container T and the bar-code reading section 516 can read the sample bar-code. In addition, when the sample container setting section 515b is moved to the aspiration position, the sample is aspirated from the set sample container T by the sample aspirating section 511.

Figure 8:
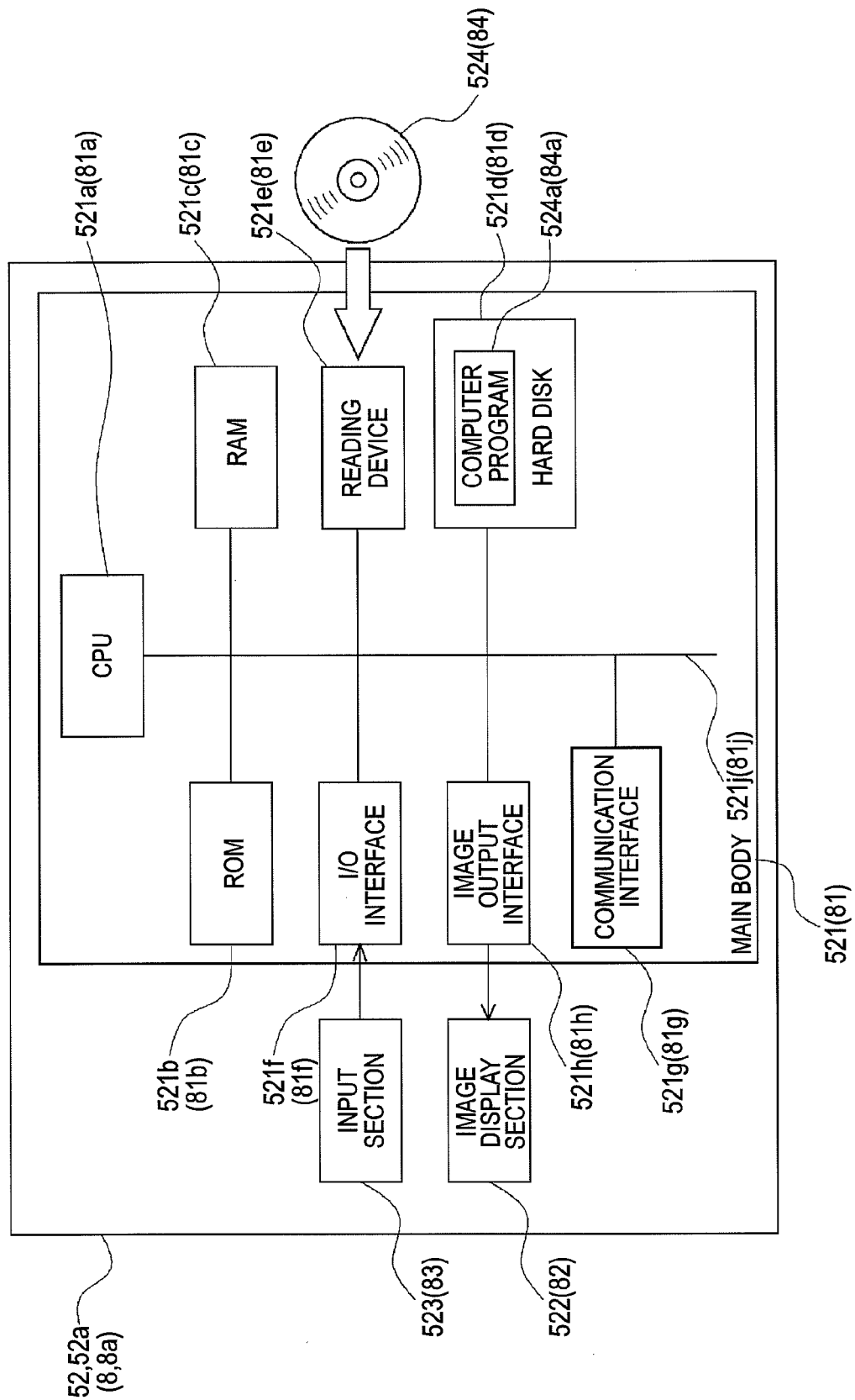
FIG. 8 is a block diagram illustrating the configuration of an information processing unit of a sample testing apparatus according to an embodiment.

Next, the configuration of the information processing unit 52 will be described. The information processing unit 52 is composed of a computer. FIG. 8 is a block diagram illustrating the configuration of the information processing unit 52. The information processing unit 52 is realized by a computer 52a. As shown in FIG. 8, the computer 52a includes a main body 521, an image display section 522 and an input section 523. The main body 521 includes a CPU 521a, a ROM 521b, a RAM 521c, a hard disk 521d, a reading device 521e, an I/O interface 521f, a communication interface 521g and an image output interface 521h. The CPU 521a, ROM 521b, RAM 521c, hard disk 521d, reading device 521e, I/O interface 521f, communication interface 521g and image output interface 521h are connected to each other by a bus 521j.

The CPU 521a can execute a computer program loaded to the RAM 521c. The CPU 521a executes a computer program 524a for testing a sample and controlling the measuring unit 51 and the first transport mechanism 31, which will be described later, so that the computer 52a functions as the information processing unit 52.

The ROM 521b is composed of a mask ROM, a PROM, an EPROM an EEPROM or the like and the computer program executed by the CPU 521a and data used for the computer program are recorded in the ROM.

The RAM 521c is composed of a SRAM, a DRAM or the like. The RAM 521c is used to read the computer program 524a recorded in the hard disk 521d. In addition, the RAM is used as an operating area of the CPU 521a when the CPU 521a executes a computer program.

In the hard disk 521d, various computer programs for execution by the CPU 521a, such as an operating system and an application program, and data which is used to execute the computer programs, are installed. The computer program 524a to be described later is also installed in the hard disk 521d.

The reading device 521e is composed of a flexible disk drive, a CD-ROM drive, a DVD-ROM drive or the like and can read the computer program or data recorded in a portable recording medium 524. In the portable recording medium 524, the computer program 524a for prompting the computer to function as the information processing unit 52 is stored. The computer 52a can read the computer program 524a from the portable recording medium 524 and install the computer program 524a in the hard disk 521d.

The computer program 524a is provided by the portable recording medium 524 and can be also provided from an external device, which is connected to the computer 52a by an electric communication line (which may be wired or wireless) to communicate therewith, through the electric communication line. For example, the computer program 524a is stored in a hard disk of a server computer on the internet and the computer 52a accesses the server computer to download the computer program and install the computer program in the hard disk 521d.

Furthermore, in the hard disk 521d, for example, a multitasking operating system such as Windows (registered trade name), which is made and distributed by Microsoft corporation in America, is installed. In the following description, the computer program 524a according to this embodiment operates on the above operating system.

The I/O interface 521f is composed of, for example, a serial interface such as USB, IEEE1394 or RS-232C, a parallel interface such as SCSI, IDE or IEEE1284, and an analog interface including a D/A converter and an A/D converter. The input section 523 composed of a keyboard and a mouse is connected to the I/O interface 521f and the user uses the input section 523 so as to input data to the computer 52a. In addition, the I/O interface 521f is connected to the three measuring units 51, 51 and 51 so as to send and receive data to and from the respective three measuring units 51, 51 and 51.

The communication interface 521g is an Ethernet (registered trade name) interface. The communication interface 521*g* is connected to the system control apparatus 8 via a LAN. Via the communication interface 521*g*, the computer 52*a* can send and receive data to and from the system control apparatus 8 connected to the LAN by using a predetermined communication protocol. In addition, the communication interface 521*g* is connected to the testing information management apparatus 9 via the LAN so as to communicate therewith.

The image output interface 521*h* is connected to the image display section 522 composed of a LCD, a CRT or the like so as to output a picture signal corresponding to the image data provided from the CPU 521*a* to the image display section 522. The image display section 522 displays an image (screen) in accordance with an input picture signal.

<Configuration of Smear Slide Preparing Apparatus 6>

The smear slide preparing apparatus 6 aspirates a blood sample so as to deliver it onto a slide glass by drops, spreads and dries the blood sample on the slide glass, and supplies a stain solution to the slide glass to stain the blood on the slide glass. In this manner, the smear slide preparing apparatus prepares a smear slide.

Figure 9:
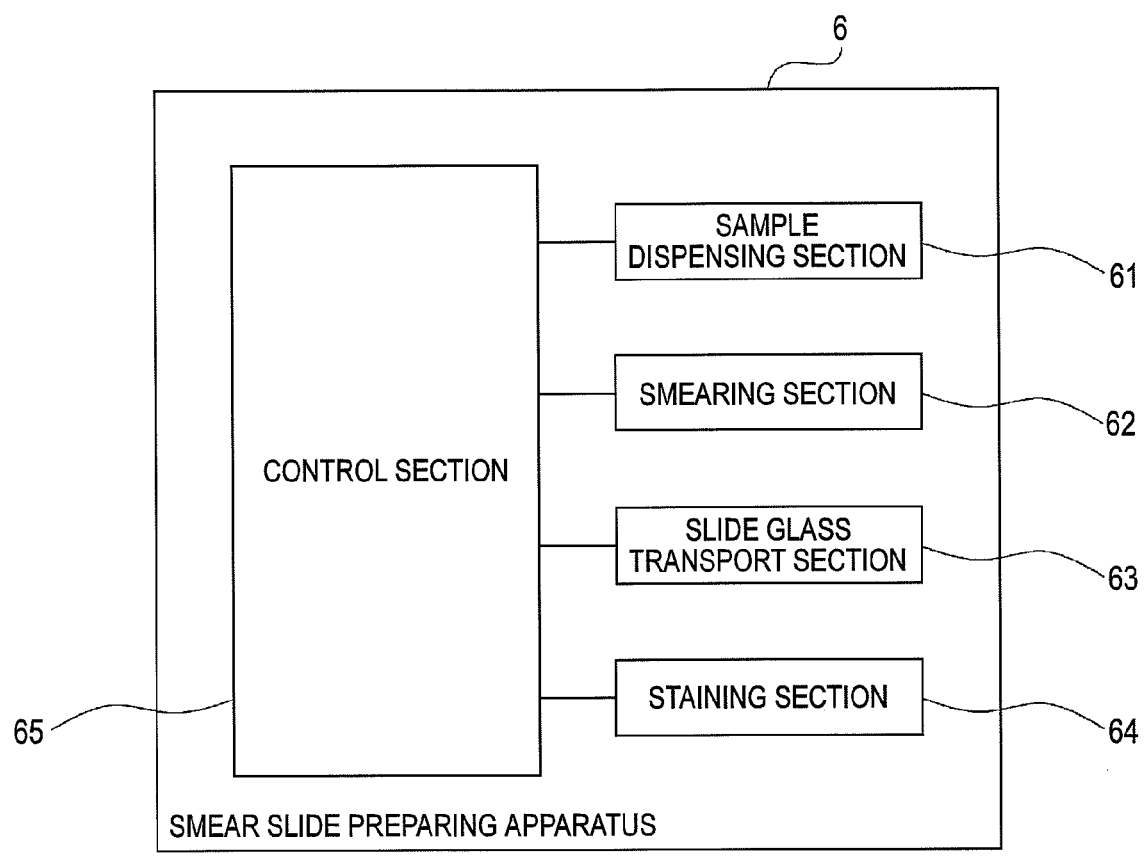
FIG. 9 is a block diagram schematically illustrating the configuration of a smear slice preparing apparatus according to an embodiment.

FIG. 9 is a block diagram illustrating the schematic configuration of the smear slide preparing apparatus 6. As shown in FIG. 9, the smear slide preparing apparatus 6 includes a sample dispensing section 61, a smearing section 62, a slide glass transport section 63, a staining section 64 and a control section 65.

The sample dispensing section 61 includes an aspiration tube (not shown) and the aspiration tube is stuck in the cap section CP of the sample container T in the sample rack L transported on the measurement line 302*a* of the sample transport apparatus 3 so as to aspirate a blood sample from the sample container T. In addition, the sample dispensing section 61 is configured to drop the aspirated blood sample onto a slide glass. The smearing section 62 is configured to smear and dry the blood sample dropped onto the slide glass and perform printing on the slide glass.

The slide glass transport section 63 is provided to accommodate the slide glass on which the blood sample is smeared by the smearing section 62 in a cassette (not shown) and to transport the cassette. The staining section 64 supplies a stain solution to the slide glass in the cassette transported to a staining position by the slide glass transport section 63. The control section 65 controls the sample dispensing section 61, the smearing section 62, the slide glass transport section 63 and the staining section 64 in accordance with a smear slide preparing instruction issued from the sample transport apparatus 3 so as to perform the above smear slide preparing operation. The smear slide prepared in this manner is delivered to a blood cell image display apparatus (not shown).

<Configuration of System Control Apparatus 8>

The system control apparatus 8 is composed of a computer and controls the entire sample testing system 1. The system control apparatus 8 receives a rack ID of the sample rack L and a sample ID of the sample held on the sample rack L from the sample putting apparatus 2, and determines a transport destination of the sample rack L.

The system control apparatus 8 is realized by a computer 8*a*. As shown in FIG. 8, the computer 8*a* includes a main body 81, an image display section 82 and an input section 83. The main body 81 includes a CPU 81*a*, a ROM 81*b*, a RAM 81*c*, a hard disk 81*d*, a reading device 81*e*, an I/O interface 81*f*, a communication interface 81*g* and an image output interface 81*h*. The CPU 81*a*, ROM 81*b*, RAM 81*c*, hard disk 81*d*, reading device 81*e*, I/O interface 81*f*, communication interface 81*g* and image output interface 81*h* are connected to each other by a bus 81*j*.

In the hard disk 81*d*, various computer programs for execution by the CPU 81*a*, such as an operating system and an application program, and data, which are used to execute the computer programs, are installed. A system control program 84*a* to be described later is also installed in the hard disk 81*d*.

The reading device 81*e* is composed of a flexible disk drive, a CD-ROM drive, a DVD-ROM drive or the like and can read the computer program or data recorded in a portable recording medium 84. In the portable recording medium 84, the system control program 84*a* for prompting the computer to function as the system control apparatus 8 is stored. The computer 8*a* can read the system control program 84*a* from the portable recording medium 84 so as to install the system control program 84*a* in the hard disk 81*d*.

The I/O interface 81*f* is composed of, for example, a serial interface such as USB, IEEE1394 or RS-232C, a parallel interface such as SCSI, IDE or IEEE1284, and an analog interface including a D/A converter and an A/D converter. The input section 83 composed of a keyboard and a mouse is connected to the I/O interface 81*f* and the user uses the input section 83 so as to input data to the computer 8*a*.

The communication interface 81*g* is an Ethernet (registered trade name) interface. The communication interface 81*g* is connected to the sample putting apparatus 2, the sample transport apparatus 3, the sample accommodating apparatus 4, the information processing unit 52 and the testing information management apparatus 9 via a LAN. Via the communication interface 81*g*, the computer 8*a* can send and receive data to and from the above respective apparatuses connected to the LAN by using a predetermined communication protocol.

Since the other configurations of the system control apparatus 8 are the same as the configurations of the above-described information processing unit 52, description thereof will be omitted.

<Configuration of Testing Information Management Apparatus 9>

The testing information management apparatus 9 is a laboratory information system (LIS). The testing information management apparatus 9 stores the measuring order and the retest order, and provides the measuring order and the retest order according to the request from other apparatuses. In addition, the testing information management apparatus 9 determines whether or not the retest is necessary based on the first-round testing result, and determines the retest items when the retest is necessary so as to generate the retest order.

Figure 10:
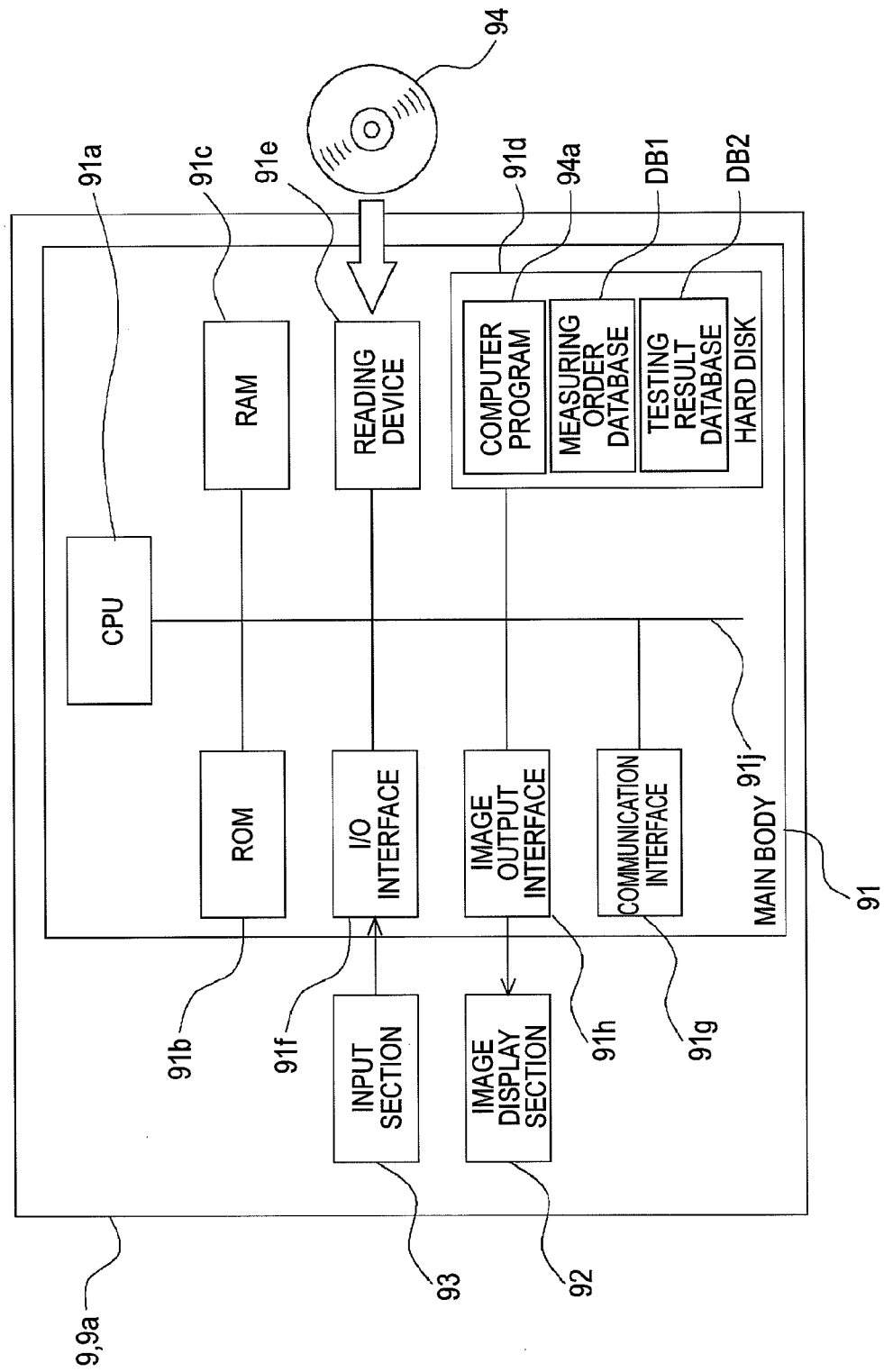
FIG. 10 is a block diagram illustrating the configuration of a testing information management apparatus according to an embodiment.

FIG. 10 is a block diagram illustrating the configuration of the testing information management apparatus 9. The testing information management apparatus 9 is realized by a computer 9*a*. As shown in FIG. 10, the computer 9*a* includes a main body 91, an image display section 92 and an input section 93. The main body 91 includes a CPU 91*a*, a ROM 91*b*, a RAM 91*c*, a hard disk 91*d*, a reading device 91*e*, an I/O interface 91*f*, a communication interface 91*g* and an image output interface 91*h*. The CPU 91*a*, ROM 91*b*, RAM 91*c*, hard disk 91*d*, reading device 91*e*, I/O interface 91*f*, communication interface 91*g* and image output interface 91*h* are connected to each other by a bus 91*j*.

In the hard disk 91*d*, various computer programs for execution by the CPU 91*a*, such as an operating system and an application program, and data which is used to execute the computer programs, are installed. A testing information management program 94*a* to be described later is also installed in the hard disk 91*d*.

In addition, a measuring order database DB1 is installed on the hard disk 91*d*. The measuring order is registered in the measuring order database DB1. The measuring order includes the sample ID and information on the measuring items of an object. Upon receiving request data for the measuring order including the sample ID from another apparatus, the testing information management apparatus 9 reads measuring data corresponding to the sample ID from the measuring order database DB1 and transmits the measuring data to the apparatus which was the request source. In addition, the retest order is also registered in the measuring order database DB1. The retest order includes the sample ID and information of the retest items. As to be described later, when the testing information management apparatus 9 generates the retest order, the retest order is registered in the measuring order database DB1. In the measuring order database DB1, information for specifying the retest order is stored by association with each retest order. Therefore, the data registered in the measuring order database DB1 can be identified as the measuring order or the retest order.

In addition, a testing result database DB2 is installed on the hard disk 91*d*. The testing result and the retesting result of the sample by the sample analysis apparatus are stored in the testing result database DB2. The testing result includes the sample ID, a variety of numerical data (RBC, PLT, HGB, WBC, NEUT, LYMPH, EO, BASO, MONO, etc.) obtained by analyzing the sample, and distribution data such as scattergrams and histograms. Upon receiving the testing result or the retesting result from the sample testing apparatus connected thereto, the testing information management apparatus 9 registers the testing result or the retesting result in the testing result database DB2. In addition, the testing information management apparatus 9 reads out the testing result or the retesting result of the sample from the testing result database DB2 according to the instruction given by an operator, and displays the testing result or the retesting result on an image display section 92. In the testing result database DB2, information for specifying the retesting result is stored by association with each retesting result data. Therefore, the data registered in the testing result database DB2 can be identified as the first-round testing result or the retesting result.

The reading device 91*e* is composed of a flexible disk drive, a CD-ROM drive, a DVD-ROM drive or the like and can read the computer program or data recorded in a portable recording medium 94. In the portable recording medium 94, the testing information management program 94*a* for prompting the computer to function as the testing information management apparatus 9 is stored. The computer 9*a* can read the testing information management program 94*a* from the portable recording medium 94 so as to install the testing information management program 94*a* in the hard disk 91*d*.

The I/O interface 91*f* is composed of, for example, a serial interface such as USB, IEEE1394 or RS-232C, a parallel interface such as SCSI, IDE or IEEE1284, and an analog interface including a D/A converter and an A/D converter. The input section 93 composed of a keyboard and a mouse is connected to the I/O interface 91*f* and the user uses the input section 93 so as to input data to the computer 9*a*.

The communication interface 91*g* is an Ethernet (registered trade name) interface. The communication interface 91*g* is connected to the sample putting apparatus 2, the sample transport apparatus 3, the sample accommodating apparatus 4, the information processing unit 52 and the system control apparatus 9 via a LAN. Via the communication interface 91*g*, the computer 9*a* can send and receive data to and from the above respective apparatuses connected to the LAN by using a predetermined communication protocol.

Since the other configurations of the testing information management apparatus 9 are the same as the configurations of the above-described information processing unit 52, description thereof will be omitted.

Hereinafter, the operation of the sample testing system 1 according to this embodiment will be described.

<Operation of Sample Putting Apparatus 2>

An operator places the sample rack L accommodating the sample containers T on the sample putting unit 21, and operates an operation panel (not shown) of the sample putting unit 21 so as to give a processing start instruction to the sample testing system 1. The control section 2*a* of the sample putting apparatus 2 receives the processing start instruction so as to start to move the sample rack L. After receiving the instruction of the analysis start, the sample rack L disposed on the sample putting apparatus 2 is detected by the sensor of the sample putting apparatus 2. Accordingly, when the sample rack L is detected by the sensor, the control section of the sample putting apparatus 2 assigns a number (hereinafter, referred to as "rack sequential number") to the sample rack L. Further, the rack sequential number is assigned on each sample rack L in an order of detection by the sensor. Thereafter, the sample rack L placed on the sample putting unit 21 moves backward on the sample putting unit 21, and then the sample rack L moves in the left direction so as to be transferred to the bar-code reading unit 22.

The control section 2*a* moves the sample rack L, which is fed to the bar-code reading unit 22, on the transport path in the left direction. Then, the rack bar-code of the sample rack L and the sample bar-code of the sample container T are read by the bar-code reader. The read rack ID and sample ID are transmitted to the system control apparatus 8 by the control section 2*a*. Next, the sample rack further moves in the left direction and the sample rack L is transported to the sample delivery unit 23. The control section 2*a* moves the sample rack L, which is received by the sample delivery unit 23, on the sample delivery unit 23. Thereafter, the sample putting apparatus 2 transmits the unloading request data including the rack ID to the system control apparatus 8, and stands by to receive the unloading instruction data transmitted from the system control apparatus 8. Upon receiving the unloading instruction data from the system control apparatus 8, the sample putting apparatus 2 unloads the sample rack L to the neighboring sample transport apparatus 3 and transmits unloading completion data to the system control apparatus 8.

<Operation of System Control Apparatus 8>

Next, the operation of the system control apparatus 8 will be described.

Measuring Order Obtaining Operation of System Control Apparatus 8

The system control apparatus 8 receives the sample ID from the sample putting apparatus 2, and makes an inquiry to the testing information management apparatus 9 for the measuring order by using the sample ID as a key so as to obtain the measuring order. Hereinafter, this operation will be described in detail.

Figure 11:
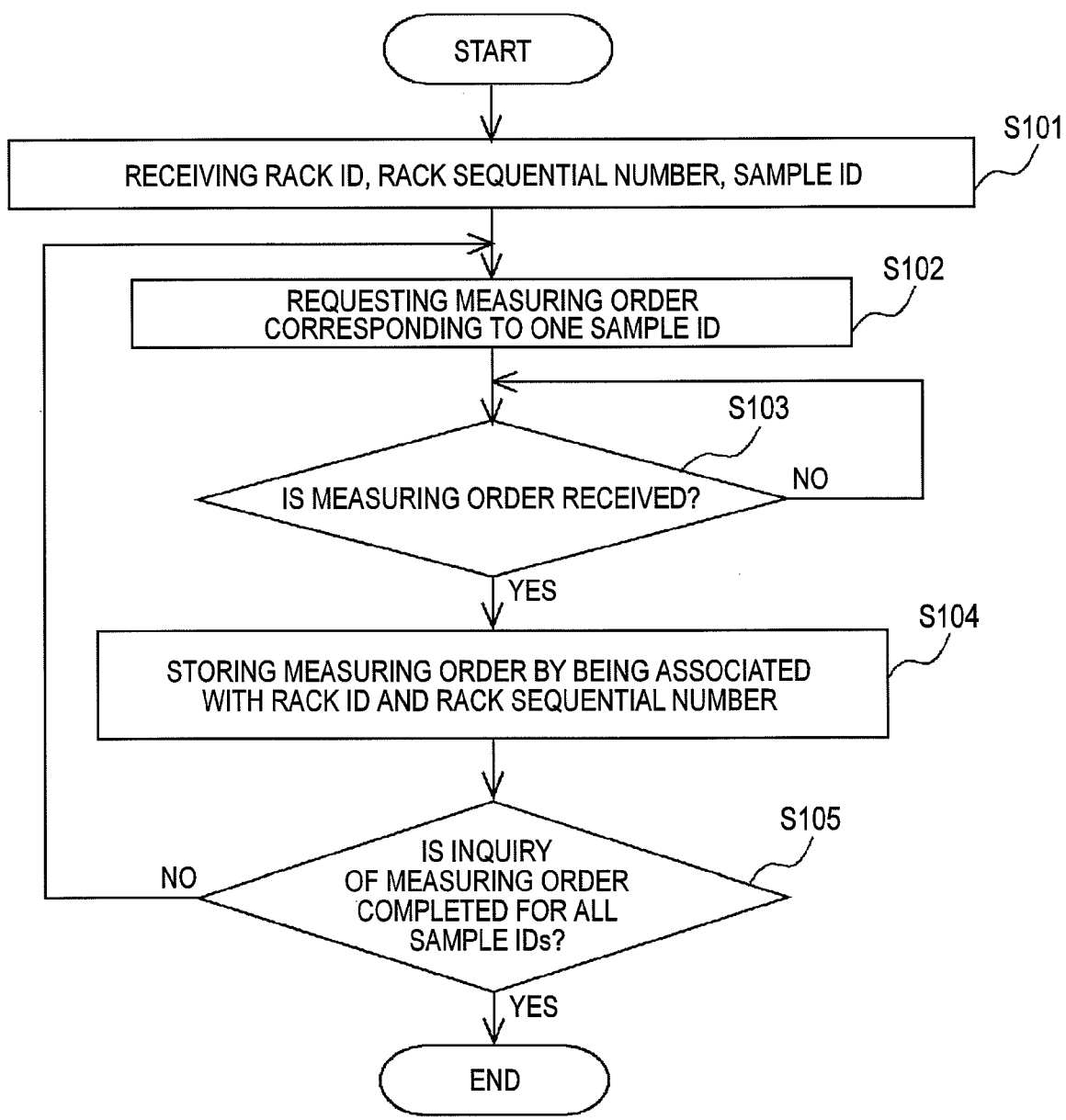
FIG. 11 is a flowchart illustrating the flow of a measuring order obtaining operation of a system control apparatus according to an embodiment.

FIG. 11 is a flowchart illustrating the flow of the measuring order obtaining operation of the system control apparatus 8. As described above, the sample putting apparatus 2 transmits the sample ID and the rack ID which are read by the bar-code reader, and the rack sequential number assigned to the sample rack L, which is specified by the rack ID, to the system control apparatus 8. The rack ID, the sample ID, and the rack sequential number are received by the communication interface 81*g* of the system control apparatus 8 (Step S101). In the CPU

81*a*, a process of Step S102 is invoked when an event occurs in which the rack sequential number, the rack ID, and the sample ID are received.

In Step S102, the CPU 81*a* transmits the order request data including one of the received sample IDs to the testing information management apparatus 9, and requests a measuring order corresponding to the sample ID from the testing information management apparatus 9 (Step S102). The CPU 81*a* stands by to receive the measuring order (NO in Step S103). When the system control apparatus 8 receives the measuring order transmitted from the testing information management apparatus 9 (YES in Step S103), the CPU associates the received measuring order with the rack ID and the rack sequential number so as to store the measuring order in the hard disk 81*d* (Step S104).

Next, the CPU 81*a* determines whether the sample IDs corresponding to the rack ID, that is, the sample IDs of all the samples accommodated in the sample rack L with the rack ID have been subjected to an measuring order inquiry (Step S105). When there is a sample ID not subjected to the measuring order inquiry (NO in Step S105), the CPU returns the process to Step S102 and requests a measuring order corresponding to the sample ID not yet subjected to the measuring order inquiry from the testing information management apparatus 9. On the other hand, when all of the sample IDs have been subjected to the measuring order inquiry (YES in Step S105), the CPU 81*a* completes the process.

First Transport Instruction Process From System Control Apparatus 8 to Sample Putting Apparatus 2

The system control apparatus 8 receives the unloading request data from the sample putting apparatus 2, determines the transport destination of the sample rack L by using the rack ID included in the unloading request data and instructs the respective apparatuses to transport the sample rack L to the determined transport destination. Hereinafter, this operation will be described in detail.

Figure 12A:
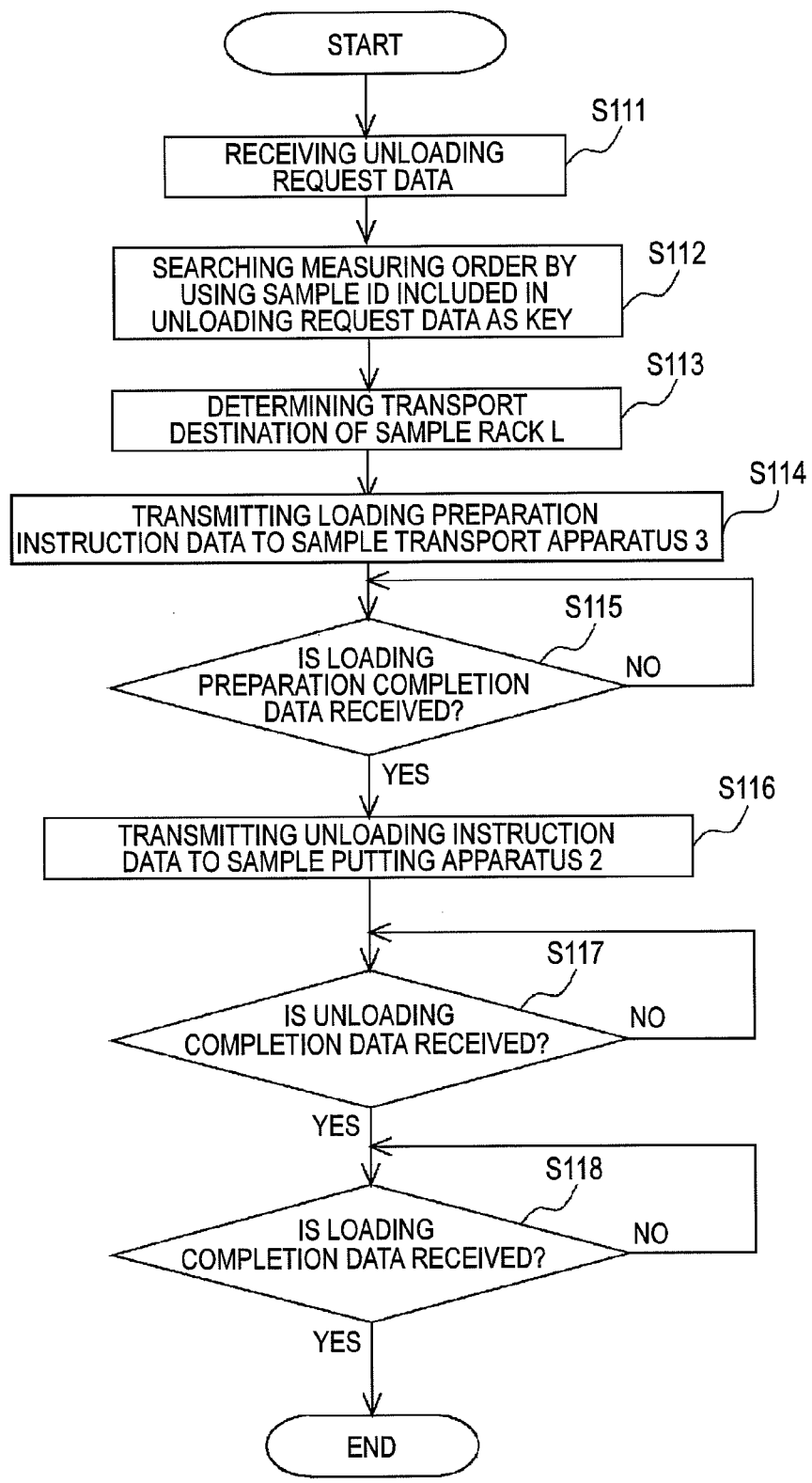
FIG. 12A is a flowchart illustrating the procedure of a first transport instruction process of a system control apparatus according to an embodiment.

FIG. 12A is a flowchart illustrating the procedure of a first transport instruction process of the system control apparatus 8. In the first transport instruction process, the transport destination of the sample rack L is determined and a transport instruction is issued to the sample transport apparatus 3 disposed in front of the measuring unit 51 on the uppermost-stream side in the transport direction. The unloading request data transmitted from the sample putting apparatus 2 is received by the communication interface 81*g* of the system control apparatus 8 (Step S111). In the CPU 81*a*, a process of Step S112 is invoked when an event occurs in which the unloading request data is received.

In Step S112, the CPU 81*a* searches the measuring order stored in the hard disk 81*d* by using the rack ID, included in the received unloading request data, as a key (Step S112). Next, the CPU 81*a* determines the transport destination of the sample rack L based on the measuring items included in each received measuring order (Step S113). In this process, in the measuring unit 51 which is not performing a measurement at that time point or the measuring unit 51 which has the smallest number of planned measurements at that time point, the measuring unit 51 which is capable of executing all the measuring items included in the measuring order is determined as a measurement destination.

Next, based on the determined transport destination, the CPU 81*a* transmits loading preparation instruction data of the sample rack L to the sample transport apparatus 3 (that is, the rightmost sample transport apparatus 3 in FIG. 1) adjacent to the sample putting apparatus 2 (Step S114). The loading preparation instruction data includes data (hereinafter, referred to as "used transport line instruction data") indicating the transport line (the first transport mechanism 31 or the second transport mechanism 32) for transporting the sample rack L in the sample transport apparatus 3, a rack sequential number of the sample rack L, a holding position in which the sample is held on the sample rack L, and a measuring order of all the samples which are held on the sample rack L. That is, when the transport destination of the sample rack L is the first transport mechanism 31 of the sample transport apparatus 3 adjacent to the sample putting apparatus 2, data indicating the first transport mechanism as the used transport line instruction data is set in the loading preparation instruction data. On the other hand, when the first transport mechanism 31 of the following sample transport apparatus 3 is determined as the transport destination, data indicating the second transport mechanism as the used transport line instruction data is set in the loading preparation instruction data. As described later, the sample transport apparatus 3 receiving the loading preparation instruction data performs an operation of preparing the transport mechanism indicated by the used transport line instruction data included in the loading preparation instruction data (an operation to receive the sample rack L), and then transmits loading preparation completion data.

The CPU 81*a* stands by to receive the loading preparation completion data from the sample transport apparatus 3 (NO in Step S115). When the loading preparation completion data is transmitted from the sample transport apparatus 3 and is received by the system control apparatus 8 (YES in Step S115), the CPU 81*a* transmits unloading instruction data of the sample rack L to the sample putting apparatus 2 (Step S116). As described above, upon receiving the unloading instruction data, the sample putting apparatus 2 unloads the sample rack L to the sample transport apparatus 3 and transmits unloading completion data. The CPU 81*a* stands by to receive the unloading completion data from the sample putting apparatus 2 (NO in Step S117). When the unloading completion data is transmitted from the sample putting apparatus 2 and is received by the system control apparatus 8 (YES in Step S117), the CPU 81*a* stands by to receive loading completion data from the sample transport apparatus 3 (NO in Step S118). When the loading completion data is transmitted from the sample transport apparatus 3 and is received by the system control apparatus 8 (YES in Step S118), the CPU 81*a* completes the process.

Second Transport Instruction Process From System Control Apparatus 8 to Sample Transport Apparatus 3

Figure 12B:
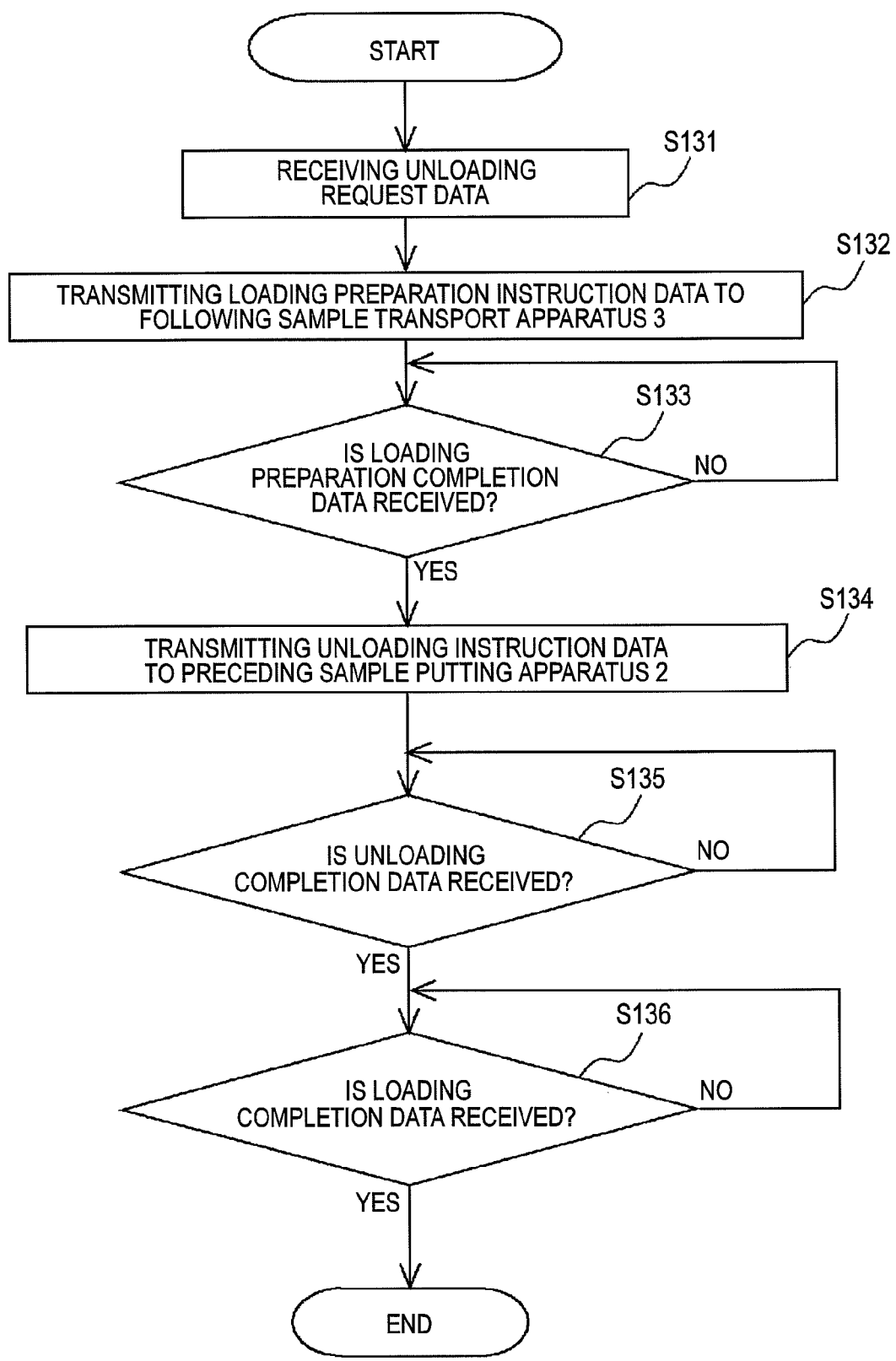
FIG. 12B is a flowchart illustrating the procedure of a second transport instruction process of a system control apparatus according to an embodiment.

Next, a second transport instruction process of transmission from the system control apparatus 8 to the sample transport apparatus 3 will be described. In the second transport instruction process, a transport instruction of the sample rack L is issued to any one of the sample transport apparatuses 3. FIG. 12B is a flowchart illustrating the procedure of the second transport instruction process. When the sample rack L transported by the sample transport apparatus 3 reaches an unloading position for unloading the sample rack L to the following sample transport apparatus 3 (or the sample transport apparatus 301), unloading request data including the rack ID of the sample rack L is transmitted from the sample transport apparatus 3. The unloading request data transmitted from the sample transport apparatus 3 is received by the communication interface 81*g* of the system control apparatus 8 (Step S131). In the CPU 81*a*, a process of Step S132 is invoked when an event occurs in which the unloading request data is received from the sample transport apparatus 3.

In Step S132, the CPU 81*a* transmits loading preparation instruction data of the sample rack L to the sample transport apparatus 3 following the present sample transport apparatus 3 based on the transport destination determined by the transport destination determining process (Step S132). Since the loading preparation instruction data is the same as the above-described loading preparation instruction data, description thereof will be omitted.

Next, the CPU 81a stands by to receive loading preparation completion data from the sample transport apparatus 3 (NO in Step S133). When the loading preparation completion data is transmitted from the sample transport apparatus 3 and is received by the system control apparatus 8 (YES in Step S133), the CPU 81a transmits unloading instruction data of the sample rack L to the preceding sample transport apparatus 3 (unloading side) (Step S134). Upon receiving the unloading instruction data, the preceding sample transport apparatus 3 unloads the sample rack L to the following sample transport apparatus 3 and transmits unloading completion data. The CPU 81a stands by to receive the unloading completion data from the preceding sample transport apparatus 3 (NO in Step S135). When the unloading completion data is transmitted from the preceding sample transport apparatus 3 and is received by the system control apparatus 8 (YES in Step S135), the CPU 81a stands by to receive loading completion data from the following sample transport apparatus 3 (NO in Step S136). When the loading completion data is transmitted from the following sample transport apparatus 3 and is received by the system control apparatus 8 (YES in Step S136), the CPU 81a completes the process.

In addition, the system control apparatus 8 also performs the same second transport instruction process on the sample transport apparatus 301 and the sample accommodating apparatus 4.

<Operation of Control Section 300 of Sample Transport Apparatus 3>

Figure 13:
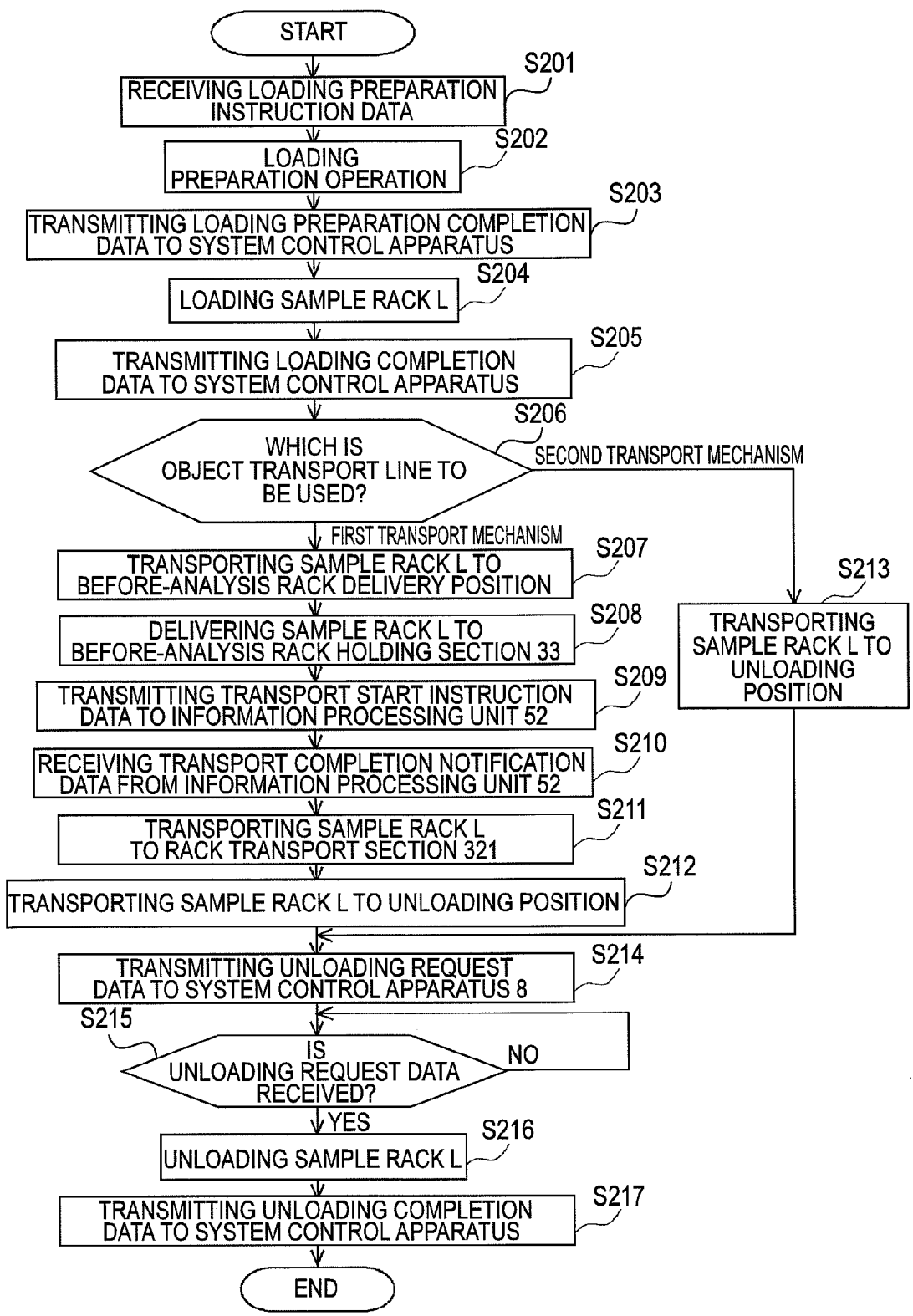
FIG. 13 is a flowchart illustrating the flow of the controlling process carried out by a control section of a sample transport apparatus according to an embodiment.

Herein, an operation of the control section 300 of the sample transport apparatus 3 disposed in front of the sample testing apparatus 5 will be described. FIG. 13 is a flowchart illustrating the flow of the process of controlling the second transport mechanism 32 by the control section 300. The loading preparation instruction data transmitted from the system control apparatus 8 is received by the control section 300 (Step S201). A transport control program which is executed by the CPU of the control section 300 is an event-driven program, and in the control section 300, a process of Step S202 is invoked when an event occurs in which the loading preparation instruction data is received.

In Step S202, the control section 300 performs a loading preparation operation by driving the belt 321a of the second transport mechanism 32 or the like (Step S202). When the loading preparation is completed, the control section 300 transmits loading preparation completion data for notifying the system control apparatus 8 that the loading preparation is completed (Step S203).

In response to the transmission of the loading preparation completion data, the sample rack L is unloaded from the preceding apparatus and is thus loaded to the second transport mechanism 32 (Step S204). When the loading of the sample rack L is completed, the control section 300 transmits loading completion data for notifying the system control apparatus 8 that the loading of the sample rack L is completed (Step S205).

Next, the control section 300 determines whether the used transport line instruction data included in the loading preparation instruction data indicates the first transport mechanism 31 or the second transport mechanism 32, that is, whether the object transport line to be used is the first measuring mechanism 31 or the second transport mechanism 32 (Step S206). In Step S206, when the used transport line instruction data included in the loading preparation instruction data indicates the first transport mechanism 31, that is, when the object transport line to be used is the first transport mechanism 31 ("first transport mechanism" in Step S206), the control section 300 controls the rack transport section 321 so as to transport the sample rack L to the before-analysis rack delivery position (step S207). Next, the control section 300 drives the rack delivery section 322 so as to send the sample rack L to the before-analysis rack holding section 33 of the first transport mechanism 31 (step S208). In addition, the control section 300 transmits transport start instruction data for instructing the transport start of the sample rack L to the information processing unit 52 (step S209).

Thereafter, as to be described later, the sample rack L is transported by the first transport mechanism 31, so that the sample is supplied to the measuring unit 51. After the measurement of all the samples held on the sample rack L is completed, the sample rack L is further transported by the first transport mechanism 31 and delivered to the after-analysis rack holding section 34. In addition, at this time, transport completion notification data for notifying the transport completion of the sample rack L by the first transport mechanism 31 is transmitted from the information processing unit 52. The transport completion notification data transmitted from the information processing unit 52 is received by the control section 300 (Step S210). In the CPU 521a, a process of Step S211 is invoked when an event occurs in which the transport completion notification data is received.

In Step S211, the control section 300 drives the stepping motor 34c so as to operate the rack sending section 34b, and thereby moves the sample rack L to the rack transport section 321 (Step S211). Next, the control section 300 drives the stepping motor 321b so as to operate the rack transport section 321, and thereby the sample rack L moves on the rack transport section 321 and reaches the unloading position for unloading the sample rack L (Step S212). Thereafter, the control section 300 moves the process to Step S214.

On the other hand, in Step S206, when the used transport line instruction data included in the loading preparation instruction data indicates the second transport mechanism 32, that is, when the second transport mechanism 32 is the object transport line to be used ("second transport mechanism" in Step S206), the control section 300 controls the rack transport section 321 so as to move the sample rack L on the rack transport section 321 and the sample rack L reaches the unloading position to be unloaded (Step S213). Thereafter, the control section 300 moves the process to Step S214.

In Step S214, the control section 300 transmits the unloading request data including the rack sequential number which is assigned to the sample rack L to the system control apparatus 8 (Step S214). Thereafter, the control section 300 stands by to receive the unloading instruction data from the system control apparatus 8 (NO in Step S215). Upon receiving the unloading instruction data (YES in Step S215), the control section drives the stepping motor 321b so as to unload the sample rack L to the neighboring sample transport apparatus 3 (Step S216), and transmits the unloading completion data to the system control apparatus 8 (Step S217). Then, the control section 300 completes the process.

<Operation of Sample Testing Apparatus 5>

Next, the operation of the sample testing apparatus 5 will be described. The information processing unit 52 controls the first transport mechanism 31 in cooperation with the sample transport apparatus 3. Hereinafter, the operation for controlling the first transport mechanism 31 of the information processing unit 52 will be described.

Figure 14A:
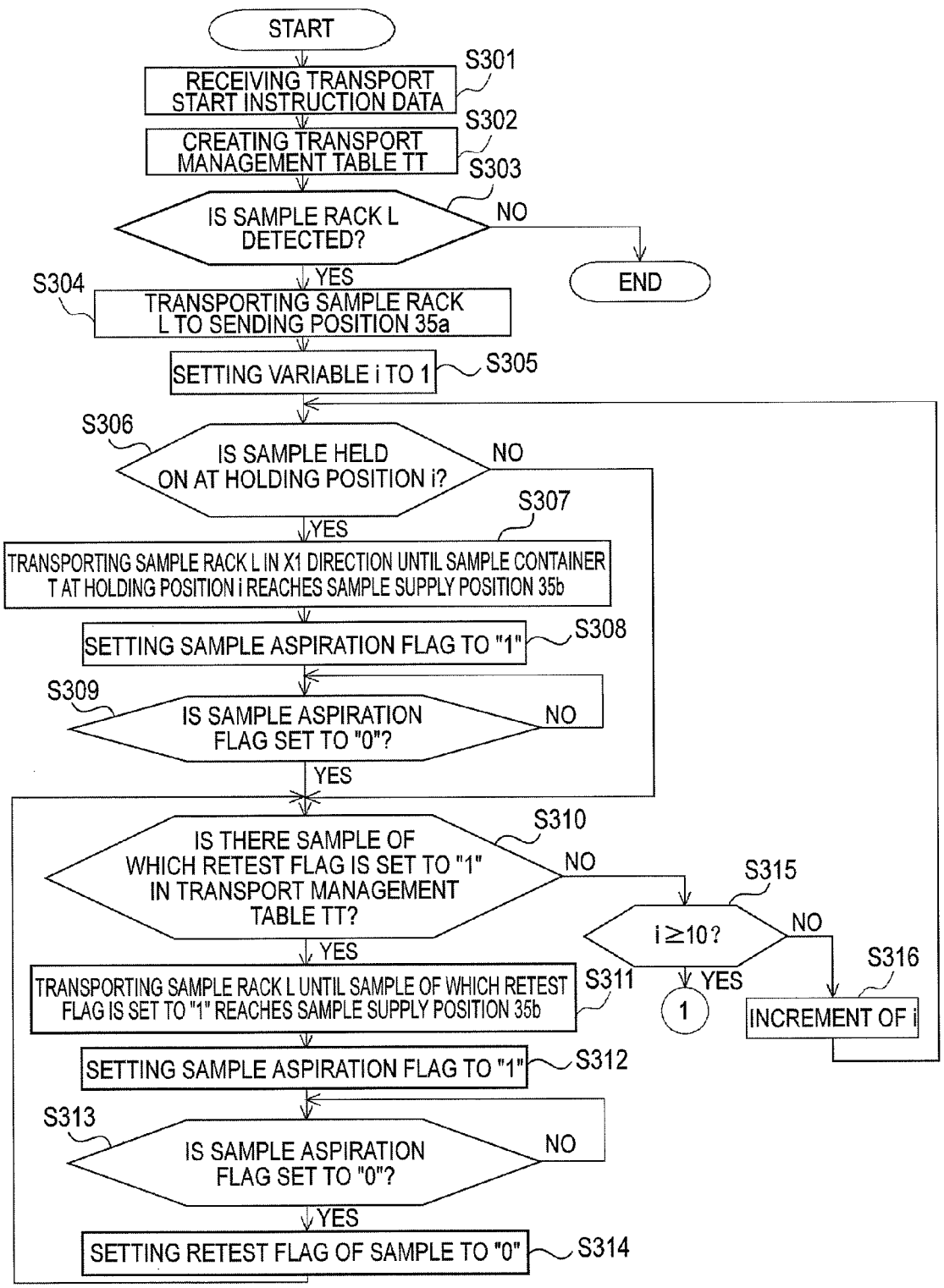
FIG. 14A is a flowchart (first half) illustrating the flow of the process for controlling a first transport mechanism carried out by an information processing unit of a sample testing apparatus according to an embodiment.
Figure 14B:
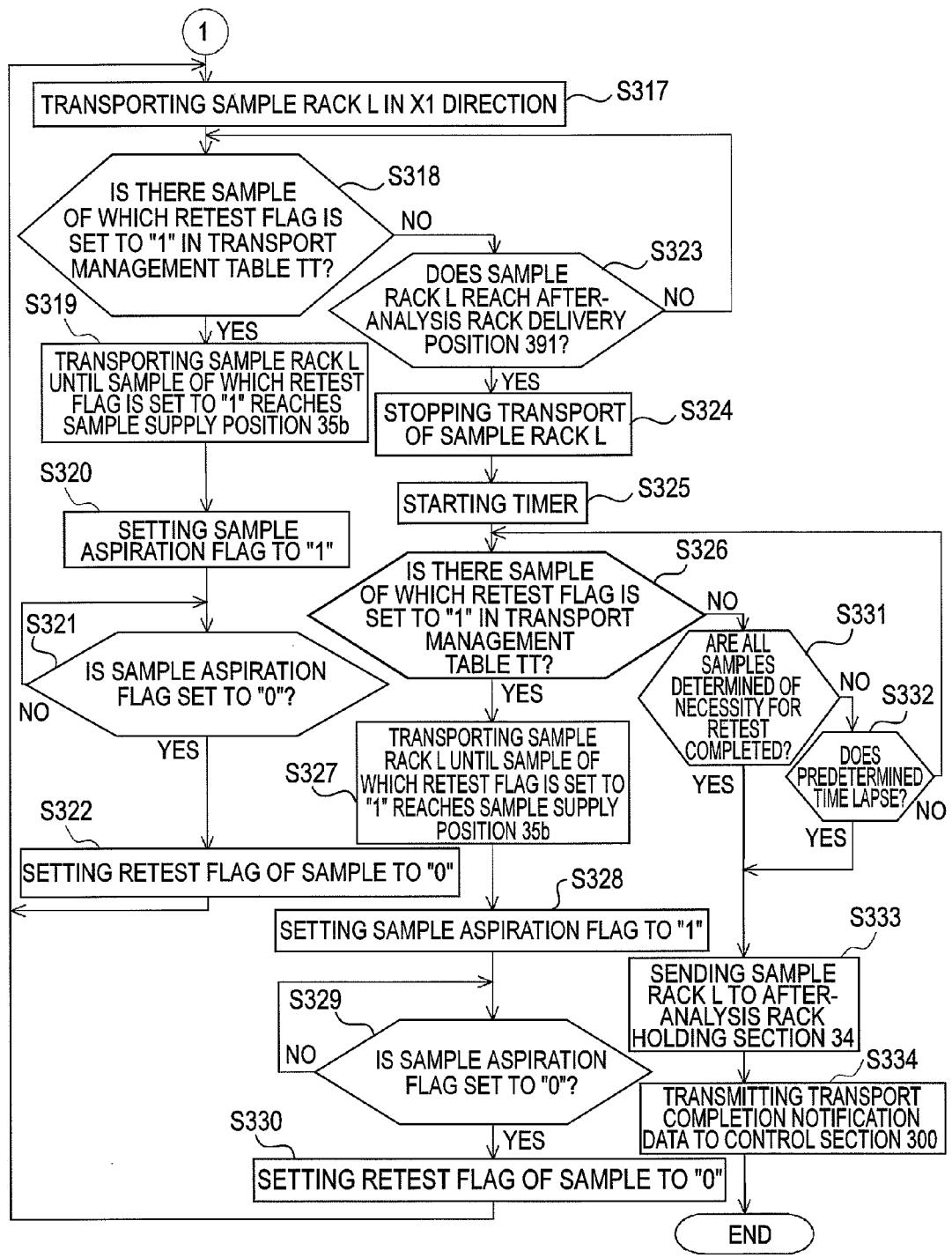
FIG. 14B is a flowchart (second half) illustrating the flow of the process for controlling a first transport mechanism carried out by an information processing unit of a sample testing apparatus according to an embodiment.

FIGS. 14A and 14B are flowcharts illustrating the flow of the process for controlling the first transport mechanism 31 by the information processing unit 52 of the sample testing apparatus 5. The transport start instruction data transmitted from the sample transport apparatus 3 is received by the communication interface 521g of the information processing unit 52 (Step S301). The transport start instruction data includes a holding position in which the sample is held on the sample rack L, and the measuring order of all the samples which are held on the sample rack L. The computer program 524a which is executed by the CPU 521a of the information processing unit 52 is an event-driven program, and in the CPU 521a, a process of Step S302 is invoked when an event occurs in which the transport start instruction data is received.

In Step S302, the CPU 521a prepares a transport management table in the RAM 521a (Step S302). FIG. 15 is a diagram schematically illustrating the structure of the transport management table. The transport management table TT is data of a table type, which is provided with a field F11 for storing holding flags by association with each of holding positions 1 to 10 of the sample rack L and a field F12 for storing retesting flags. The holding flag is a flag showing whether or not the sample container T is held at a corresponding holding position. When the sample container T is held at the corresponding holding position, "1" is stored, and when the sample container T is not held at the corresponding holding position, "0" is stored. On the other hand, each of the retest flags is a flag showing whether or not the retest is necessary. When "0" is set, it shows that the retest is not necessary for the sample, and when "1" is set, it shows that the retest is necessary. In the process of Step S302, the holding flag corresponding to the holding position at which the sample is held on the sample rack L is set to "1", and the holding flag corresponding to the holding position at which the sample is not held is set to "0".

As described above, when the sample rack L is sent to the rack detection position 33a of the before-analysis rack holding section 33 by the rack delivery section 322, the sample rack L is detected by the rack sensor 37. The CPU 521a determines whether or not the sample rack L is detected by the rack sensor 37 (Step S303). When the sample rack L is not detected (NO in Step S303), the CPU completes the process. On the other hand, when the sample rack L is detected (YES in Step S303), the CPU 521a drives the stepping motor 33c so as to operate the rack delivery section 33b, and thereby the sample rack L moves on the before-analysis rack holding section 33 and the sample rack L is transported to the sending position 35a (Step S304).

Next, the CPU 521a sets a variable i, which indicates the holding position of the sample container T in the sample rack L, to 1 (Step S305), and determines whether or not the sample is held at the holding position i with reference to the received transport start instruction data (Step S306). When the sample is held at the holding position i (YES in Step S306), the CPU 521a drives the stepping motor 351e so as to operate the rack transport section 35, and thereby moves the sample rack L, which has reached the sending position 35a, in the direction X1 until the sample container T at the holding position i reaches the sample supply position 35b (Step S307), and then a sample aspiration flag provided in the RAM 521c is set to "1" (Step S308). Therefore, the sample container T held at the holding position i is positioned at the sample supply position 35b, and the sample is aspirated as to be described later. Further, an initial value of the sample aspiration flag is "0". As to be described later, the sample aspiration flag is set to "0" once again after the aspiration of the sample is completed and the sample container T is returned to the sample rack L by the hand section 515a. The CPU 521a stands by until the sample aspiration flag is set to "0" (NO in Step S309). When the sample aspiration flag is set to "0" (YES in Step S309), the CPU moves the process to Step S310.

On the other hand, when the sample is not held at the holding position i in Step S306 (NO in Step S306), the CPU 521a moves the process to Step S310. In Step S310, the CPU 521a determines whether or not there is a sample of which the retest flag is set to "1" with reference to the transport management table TT stored in the RAM 521c (Step S310).

In Step S310, when there is a sample of which the retest flag is set to "1" (YES in Step S310), the CPU 521a drives the stepping motor 352e so as to operate the rack transport section 35, and thereby moves the sample rack L in the direction X2 until the sample of which the retest flag is set to "1" reaches the sample supply position 35b (Step S311), and sets the sample aspiration flag to "1" (Step S312). In the process of Step S311, since the sample for which it has been determined whether or not the retest is necessary is always subjected to the measurement (first-round test) earlier than the sample (which is recently subjected to the first-round test) on the holding position i, the sample of the retest object is transported in the direction X2. Thereafter, the CPU 521a stands by until the sample aspiration flag is set to "0" (NO in Step S313). When the sample aspiration flag is set to "0" (YES in Step S313), the CPU sets the retest flag of the sample to "0" (Step S314), and the process returns to Step S310.

In Step S310, when there is no sample of which the retest flag is set to "1" (NO in Step S310), the CPU 521a determines whether or not the variable i is equal to or greater than 10 (Step S315). When the variable i is less than 10 (NO in Step S315), the variable i is incremented by 1 (Step S316), the process returns to Step S306.

By the above-mentioned processes of Step S310 to Step S314, before the first-round test is completed on all of the samples held on the sample rack L, when it is determined that the sample held on the sample rack L, which has completed the first-round test already, needs to be subjected to the retest, the sample which is determined as needing to be subjected to the retest is transported in the direction X2 so as to reach the sample supply position 35b and the retest of the sample is performed. Thereafter, the sample rack L is transported in the direction X1 once again, and the samples not yet subjected to the first-round test are subjected to the first-round test.

In Step S315, when the variable i is equal to or greater than 10 (YES in Step S315), the CPU 521a drives the stepping motor 351e of the rack transport section 35 so as to move the sample rack L in the direction X1 (Step S317). Therefore, the sample rack L in which the first-round test has been completed for all the samples held thereon is transported in the direction X1.

Next, the CPU 521a determines whether or not there is a sample of which the retest flag is set to "1" with reference to the transport management table TT which is stored in the RAM 521c (Step S318). In Step S318, when there is a sample of which the retest flag is set to "1" (YES in Step S318), the CPU 521a drives the stepping motor 352e so as to operate the rack transport section 35, and thereby moves the sample rack L in the direction X2 until the sample of which the retest flag is set to "1" reaches the sample supply position 35b (Step S319), and the sample aspiration flag is set to "1" (Step S320). In the process of Step S319, all of the samples held on the sample rack L have completed the first-round test, and the sample rack L is in the middle of being transported toward the after-analysis rack delivery position 391. Therefore, when there is a sample of which the retest flag is set to "1" at this point of time, in order to position the sample of the retest object at the sample aspiration position 35b, the sample is transported in the direction X2. After the process of Step S320, the CPU 521a stands by until the sample aspiration flag is set to "0" (NO in Step S321), when the sample aspiration flag is set to "0" (YES in Step S321), the CPU sets the retest flag of the sample to "0" (Step S322), and the process returns to Step S317. Therefore, the sample rack L is transported in the direction X1 once again.

In Step S318, when there is no sample of which the retest flag is set to "1" (NO in Step S318), the CPU 521a determines whether or not the sample rack L reaches the after-analysis rack delivery position 391 (Step S323). In the process, by detecting the sample rack L at the after-analysis rack delivery position 391 by the rack sensor 391a, it is determined that the sample rack L reaches the after-analysis rack delivery position 391. In Step S323, when the sample rack L does not reach the after-analysis rack delivery position 391 (NO in Step S323), the process returns to Step S318. On the other hand, in Step S323, when the sample rack L reaches the after-analysis rack delivery position 391 (YES in Step S323), the CPU 521a stops the stepping motor 351e so as to stop transporting the sample rack L (Step S324). Therefore, the sample rack L is held on in a state of positioning at the after-analysis rack delivery position 391.

Next, the CPU 521a starts a timer (Step S325). Subsequently, the CPU 521a determines whether or not there is a sample of which the retest flag is set to "1" with reference to the transport management table TT which is stored in the RAM 521c (Step S326). That is, the CPU 521a determines whether or not the retest flag of each sample is set to "1" in the transport management table TT so as to determine whether or not the sample needs to be subjected to the retest. In Step S326, when there is a sample of which the retest flag is set to "1" (when there is a sample which needs to be subjected to the retest) (YES in Step S326), the CPU 521a drives the stepping motor 352e so as to operate the rack transport section 35, and thereby moves the sample rack L in the direction X2 until the sample of which the retest flag is set to "1" reaches the sample supply position 35b (Step S327), and sets the sample aspiration flag to "1" (Step S328). When the process of Step S327 is completed, the sample rack L is in a state of positioning at the after-analysis rack delivery position 391. Therefore, when there is a sample of which the retest flag is set to "1" at this point of time, in order to position the sample of the retest object at the sample aspiration position 35b, the sample is transported in the direction X2. After the process of Step S328, the CPU 521a stands by until the sample aspiration flag is set to "0" (NO in Step S329). When the sample aspiration flag is set to "0" (YES in Step S329), the retest flag of the sample is set to "0" (Step S330), and the process returns to Step S317. Therefore, the sample rack L is transported in the direction X1 once again.

In Step S326, when there is no sample of which the retest flag is set to "1" (when there is no sample which needs to be subjected to the retest) (NO in Step S326), the CPU 521a determines whether or not it has been completely determined whether or not the retest is necessary for all of the samples held on the sample rack L (Step S331). In the process, when the retest flags corresponding to all the holding positions in which the holding flags are set to "1" are set to "0" in the transport management table TT, it is determined that it has been completely determined whether or not the retest is necessary for all the samples held on the sample rack L. When the retest flag corresponding to even one of the respective holding positions in which the holding flags are set to "1" is not set to "0", it is determined that it has not been completely determined whether or not the retest is necessary for at least one of the samples held on the sample rack L.

In Step S331, when it is determined that it has not been completely determined whether or not the retest is necessary for at least one of the samples held on the sample rack L (NO in Step S331), the CPU 521a determines whether or not a predetermined period of time has lapsed from the point of starting the timer in Step S325 (Step S332). When the predetermined period of time has not lapsed (NO in Step S332), the CPU 521a moves the process to Step S326. By repeatedly carrying out the processes of Steps S326, S331, and S332, as long as the predetermined period of time has lapsed from the point of starting the timer, the CPU 521a keeps the sample rack L waiting at the after-analysis rack delivery position 391 until the sample, for which it is not completely determined whether or not the retest is necessary among the samples held on the sample rack L, is completely determined as to whether or not the retest is necessary.

In Step S331, when all the samples held on the sample rack L are completely determined as to whether or not the retest is necessary (YES in Step S331), the CPU 521a drives the stepping motor 39a so as to operate the rack delivery section 39, and delivers the sample rack L to the after-analysis rack holding section 34 (Step S333). Further, in Step S332, even when it is determined that the predetermined period of time has lapsed from the point of time when the timer starts in Step S325 (NO in Step S332), the CPU 521a calls a time-out to move the process to Step S333 and delivers the sample rack L to the after-analysis rack holding section 34. Thereafter, the CPU 521a transmits the transport completion notification data for notifying the transport completion of the sample rack L by the first transport mechanism 31 to the control section 300 of the sample transport apparatus 3 (Step S334), and completes the process. As described above, the control section 300 of the sample transport apparatus 3 which receives the transport completion notification data transports the sample rack L so as to be unloaded to the following apparatus.

Figure 16A:
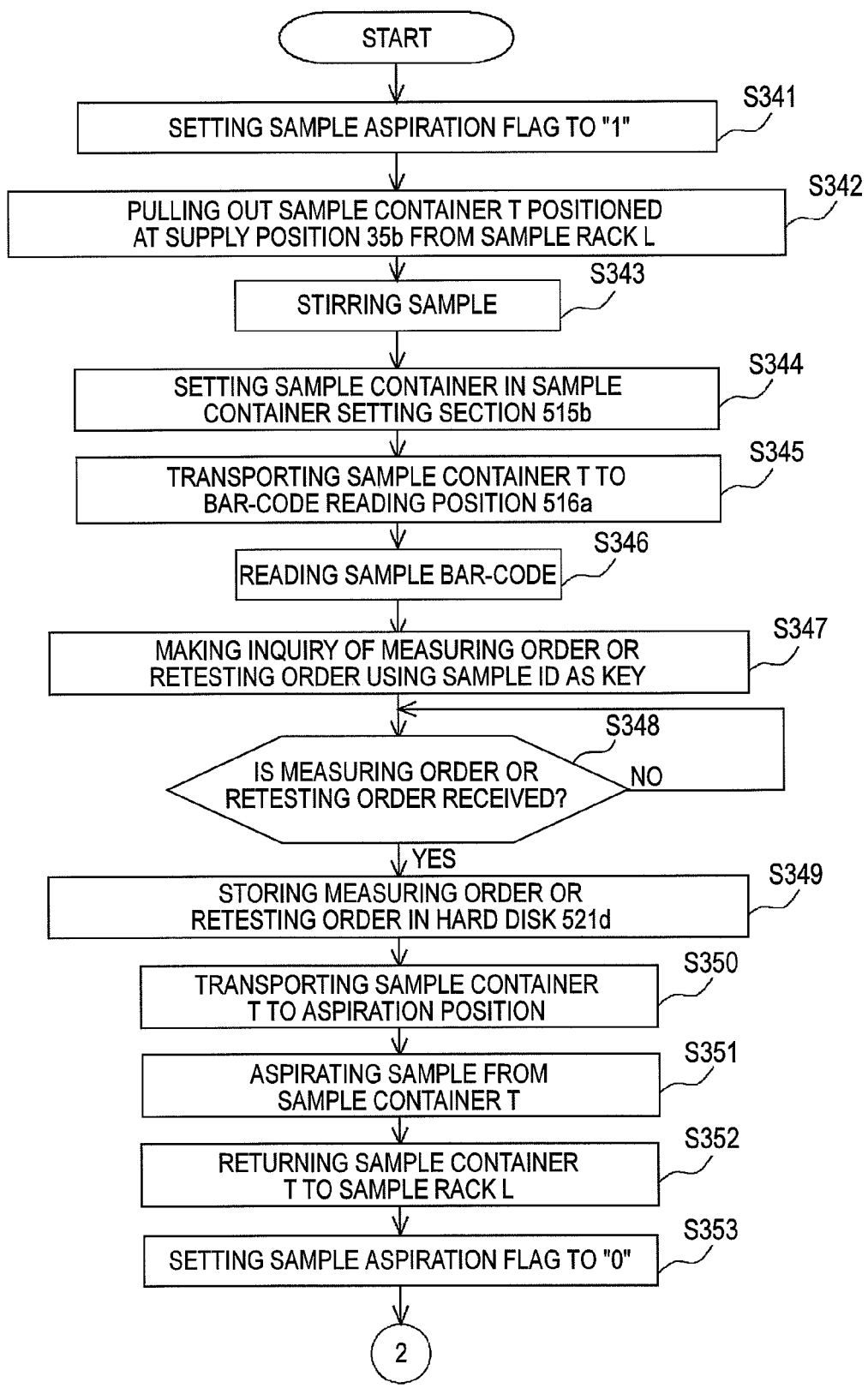
FIG. 16A is a flowchart (first half) illustrating the procedure of a testing process of a sample carried out by an information processing unit of a sample testing apparatus according to an embodiment.
Figure 16B:
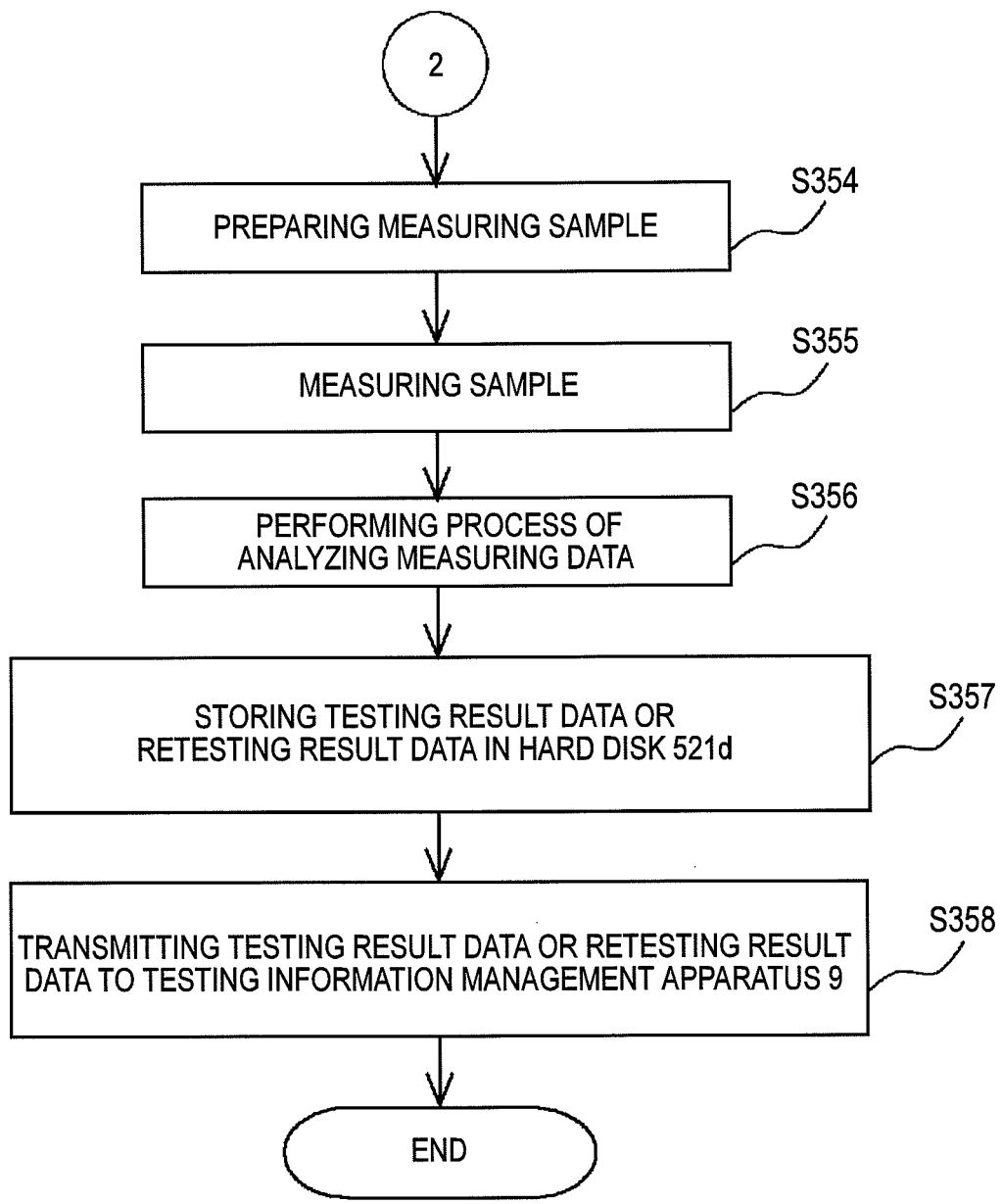
FIG. 16B is a flowchart (second half) illustrating the procedure of a testing process of a sample carried out by an information processing unit of a sample testing apparatus according to an embodiment.

Next, the testing operation (analysis operation) of the sample by the sample testing apparatus 5 will be described. FIGS. 16A and 16B are flowcharts illustrating the procedure of the testing process of the sample by the information processing unit 52 of the sample testing apparatus 5 according to this embodiment. First, the CPU 521a of the information processing unit 52 periodically checks the sample aspiration flag of the RAM 521c. In the CPU 521a, when an event occurs in which the sample aspiration flag is set to "1" (Step S341), the process of Step 342 is invoked.

In Step S342, the CPU 521a controls the sample container transport section 515 so as to pull the sample container T at the sample supply position 35b out of the sample rack L (Step S342) and controls the hand section 515a so as to oscillate the sample container T to thereby stir the sample in the sample container (Step S343). Next, the CPU 521a controls the hand section 515a so as to set the sample container T in the sample container setting section 515b (Step S344) and further controls the sample container transport section 515 so as to transport the sample container T to the bar-code reading position 516a (Step S345). Next, the CPU 521a reads the sample bar-code of the sample container T by the bar-code reading section 516 to obtain the sample ID (Step S346). Further, the CPU 521a transmits order request data including the sample ID to the testing information management apparatus 9 via the communication interface 521g (Step S347) so as to make a measuring order or retesting order inquiry. The retesting order is data which is generated when the testing result of the sample is analyzed by the testing information management apparatus 9 and it is determined that the retest is necessary, and includes the sample ID and data indicating items (retest items) to be carried out in the retest.

Thereafter, the CPU 521*a* stands by to receive the measuring order or the retesting order (NO in Step S348). When the measuring order or the retesting order transmitted from the testing information management apparatus 9 is received by the communication interface 521*g* of the information processing unit 52 (YES in Step S348), the received measuring order or retesting order is stored in the hard disk 521*d* (Step S349).

Next, the CPU 521*a* controls the sample container transport section 515 so as to transport the sample container T to the aspiration position (Step S350), and controls the sample aspirating section 511 so as to aspirate an amount of the sample necessary for the measuring item included in the stored measuring order or the retest item included in the retesting order from the sample container T (Step S351). After the aspiration of the sample is completed, the CPU 521*a* controls the sample container transport section 515 such that the sample container T returns to the sample rack L (Step S352), and sets the sample aspiration flag to "0" (Step S353). Accordingly, the sample rack L is transported by the rack transport section 35 as described above.

In addition, the CPU 521*a* controls the sample preparing section 512 so as to prepare a measurement sample in accordance with the measuring items (Step S354) and supplies the measurement sample to the detecting section 513 so as to perform the sample measurement by the detecting section 513 (Step S355). In this manner, the CPU 521*a* obtains measuring data output from the detecting section 513. The CPU 521*a* performs a process of analyzing the measuring data (Step S356), classifies the blood cells included in the sample and counts the number of blood cells for each type so as to create a scattergram in which the classified blood cells are color-coded for each type. The testing result data or retesting result data generated by the measuring data analyzing process is stored together with the patient information and the like included in the measuring order in the hard disk 521*a* (Step S357) and is transmitted to the testing information management apparatus 9 (Step S358). When the first-round testing result data is transmitted, the testing information management apparatus 9 integrates the testing result data with the above-mentioned measuring order and stores the result thereof in the hard disk. In addition, the necessity for the retest is determined. The sample which is determined as needing the retest is further determined regarding the retest item. In addition, the testing information management apparatus 9 registers the testing result data or the retesting result data which is transmitted as described above in the testing result database DB1. After the process of Step S358 is completed, the CPU 521*a* completes the process.

Next, a necessity-for-retest determination notification receiving process will be described. FIG. 17 is a flowchart illustrating the flow of the necessity-for-retest determination notification receiving process carried out by the information processing unit 52. By the analysis process of the testing result data carried out by the testing information management apparatus 9 to be described later, when it is determined whether or not the retest of the sample is necessary, the necessity-for-retest determination notification data is transmitted from the testing information management apparatus 9. The necessity-for-retest determination notification data is data provided for each sample and shows whether or not the retest is necessary. That is, when it is determined that the retest is necessary for a sample, the testing information management apparatus 9 transmits the necessity-for-retest determination notification data which includes the sample ID and information indicating that the retest is necessary. On the other hand, when it is determined that the retest is not necessary for a sample, the testing information management apparatus 9 transmits the necessity-for-retest determination notification data which includes the sample ID and information indicating that the retest is not necessary.

When the necessity-for-retest determination notification data is transmitted from the testing information management apparatus 9, the necessity-for-retest determination notification data is received by the communication interface 521*g* of the information processing unit 52 (Step S361). In the CPU 521*a*, when an event occurs in which the necessity-for-retest determination notification data is received, the process of Step S362 is invoked.

In Step S362, the CPU 521*a* determines whether or not the received necessity-for-retest determination notification data shows that the retest is necessary (Step S362). In Step S362, when the necessity-for-retest determination notification data shows that the retest is necessary (YES in Step S362), the CPU 521*a* obtains a holding position in which the sample with the corresponding sample ID is held on the sample rack L, sets the retest flag corresponding to the obtained holding position in the transport management table TT to "1" (Step S363), and completes the process.

On the other hand, in Step S362, when the necessity-for-retest determination notification data shows that the retest is not necessary (NO in Step S362), the CPU 521*a* obtains the same holding position as in Step S363, sets the retest flag in the transport management table TT, which corresponds to the obtained holding position to "0" (Step S363), and completes the process.

As described above, the transport management table TT is updated by the necessity-for-retest determination notification process. The sample relating to the holding position in which the retest flag is set to "1" by the process is transported to the sample supply position 35*b* by the above-mentioned transport control, and the retest of the sample is performed. On the other hand, the sample relating to the holding position in which the retest flag is set to "0" is not transported to the sample supply position 35*b*, and the retest of the sample is not performed.

<Operation of Testing Information Management Apparatus 9>

The testing information management apparatus 9 receives a measuring order inquiry from the information processing unit 52 and transmits the measuring order. In addition, the testing information management apparatus 9 transmits the retesting order regarding the sample of which the retesting order exists. Hereinafter, the measuring order providing process of the testing information management apparatus 9 will be described.

Figure 18:
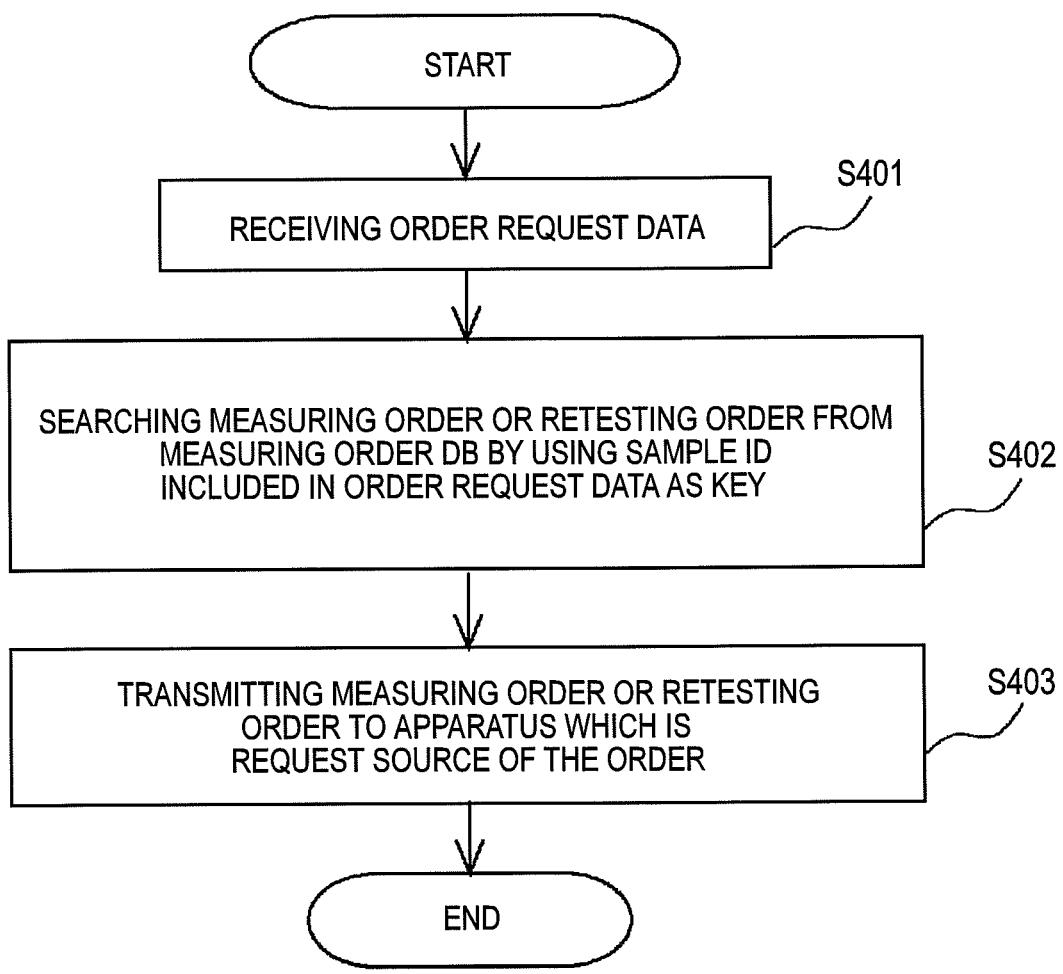
FIG. 18 is a flowchart illustrating the flow of a measuring order providing process carried out by a testing information management apparatus according to an embodiment.

FIG. 18 is a flowchart illustrating the flow of the measuring order providing process carried out by the testing information management apparatus 9. The order request data transmitted from the information processing unit 52 is received by the communication interface 91*g* of the testing information management apparatus 9 (Step S401). The order request data includes the sample ID of the sample which is necessary for the measuring order or the retesting order. The testing information management program 94*a* executed by the CPU 91*a* of the testing information management apparatus 9 is an event-driven program, and in the CPU 91*a*, a process of Step S402 is invoked when an event occurs in which the order request data is received.

In Step S402, the CPU 91*a* searches the measuring order or the retesting order which corresponds to the sample ID included in the received order request data from the measuring order database DB1 (Step S402). In this process, when there is a measuring order corresponding to the sample ID and but no retesting order, the measuring order is read from the measuring order database DB1. When there is a retesting order corresponding to the sample ID, the retesting order is read from the measuring order database DB1.

Next, the CPU 91a transmits the read measuring order or retesting order to the information processing unit 52, which is the request source of the order, via the communication interface 91g (Step S403), and completes the process.

In addition, the testing information management apparatus 9 receives the testing result data or retesting result data which is transmitted from the information processing unit 52, and stores the received testing result data or retesting result data in the testing result database DB2. In addition, when the received data corresponds to the first-round testing result data, the testing information management apparatus 9 determines whether or not the retest is necessary based on the testing result data. The sample for which it is determined that the retest is necessary is further determined regarding the retest items.

Figure 19:
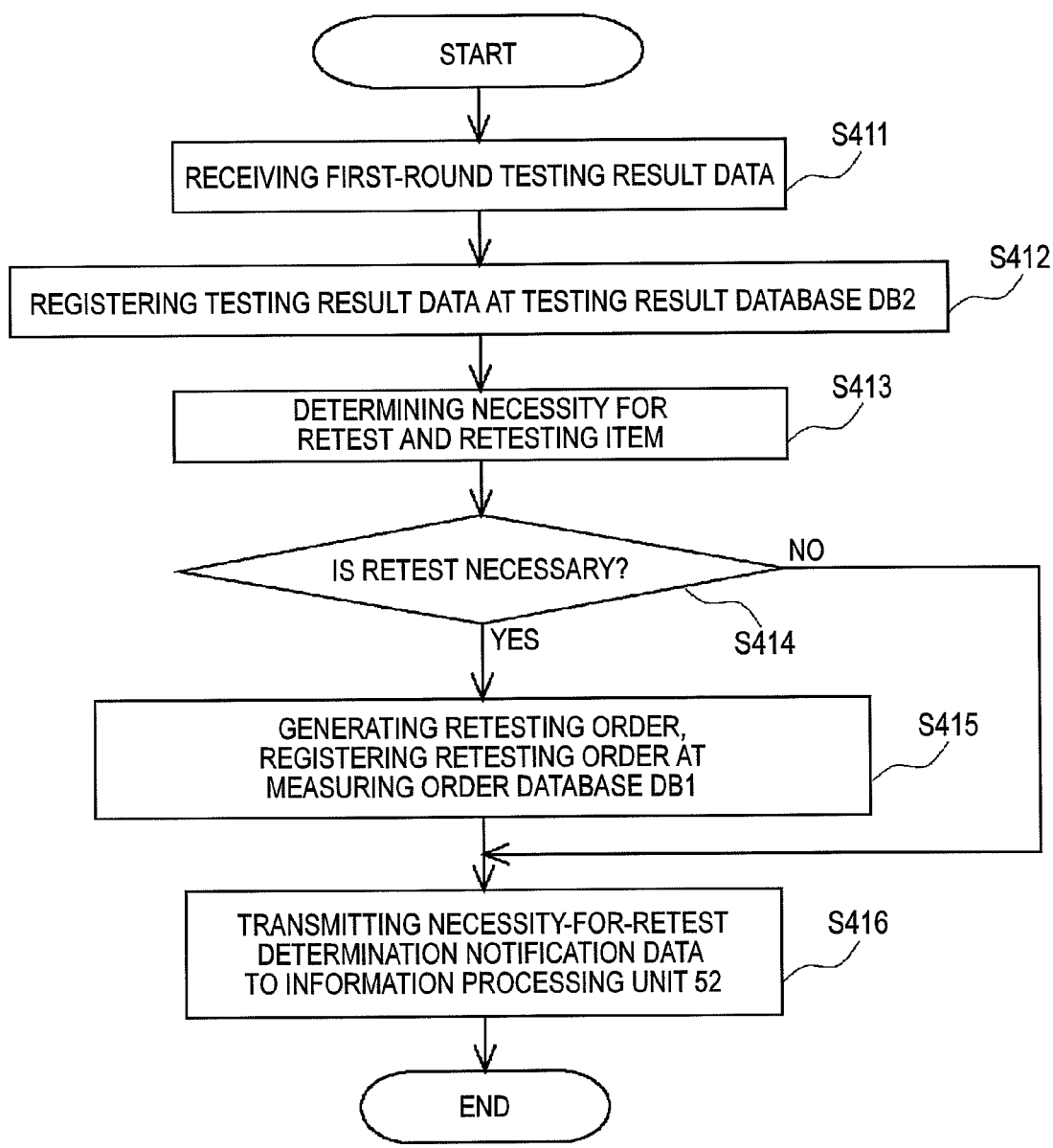
FIG. 19 is a flowchart illustrating the flow of a test result receiving process carried out by a testing information management apparatus according to an embodiment.

FIG. 19 is a flowchart illustrating the flow of the test result receiving process carried out by a testing information management apparatus 9. The testing result data transmitted from the information processing unit 52 is received by the communication interface 91g of the testing information management apparatus 9 (Step S411). The testing result data includes information showing that the data is the first-round testing result. The retesting result data includes information showing that the data is the retesting result. Therefore, by confirming the content of the data, it is possible to determine whether the data is the first-round testing result or the retesting result data. In the CPU 91a of the testing information management apparatus 9, the process of Step S412 is invoked when an event occurs in which the first-round testing result data is received.

In Step S412, the CPU 91a stores the received testing result data in the testing result database DB2 (Step S412). Next, the CPU 91a determines whether or not the sample needs to be subjected to the retest based on the testing result data stored in the testing result database DB2, and when it is determined that the sample needs to be subjected to the retest, the CPU makes a determination regarding the retest items (Step S413). In this process, the CPU determines the necessity for the retest by comparing a measurement value (numerical data) included in the testing result with a predetermined reference value. The reference value shows a normal range of the measurement value, and is provided for each measuring item. If a measurement value of a measurement item is within the reference value, it is determined that the retest is not necessary for the sample. When a measurement value exceeds the reference value, it is determined that the retest is necessary for the sample. In addition, when it is determined that the retest is necessary, the retest items are determined. For example, for the measurement of a CBC+DIFF item in the first-round test, if a numerical value of the white blood cell (WBC) obtained in the first-round test is within a first reference range (normal range), it is determined that the retest is not necessary. On the other hand, if the numerical value of the white blood cell obtained in the first-round test exceeds the first reference range and is within a second reference range (pseudo-abnormal range) larger than the first reference range, the CBC+DIFF item is determined as the retest item similarly to the first-round test. In addition, if the numerical value of the white blood cell obtained in the first-round test exceeds the second reference range and is within a third reference range (abnormal range) larger than the second reference range, an item group in which a PLT-O item is added to the CBC+DIFF item as the measurement item of the first-round test is determined as the retest item.

Next, the CPU 91a determines whether or not it is determined that the retest is necessary by the above-mentioned process of Step S413 (Step S414). When it is determined that the retest is necessary (YES in Step S414), the CPU generates the retesting order including the sample ID and the determined retest item, stores the retesting order in the measuring order database DB1 (Step S415), and moves the process to Step S416. On the other hand, when it is determined that the retest is not necessary in Step S413 (NO in Step S414), the CPU 91a moves the process to Step S416.

In Step S416, the CPU 91a transmits the necessity-for-retest determination notification data to the communication interface 91g (Step S416). In this process, when it is determined that the retest is necessary in Step S413, the CPU transmits the necessity-for-retest determination notification data indicating that the retest is necessary. When it is determined that the retest is not necessary in Step S413, the CPU transmits the necessity-for-retest determination notification data indicating that the retest is not necessary. After the process of Step S416, the CPU 91a completes the testing result receiving process.

Figure 20:
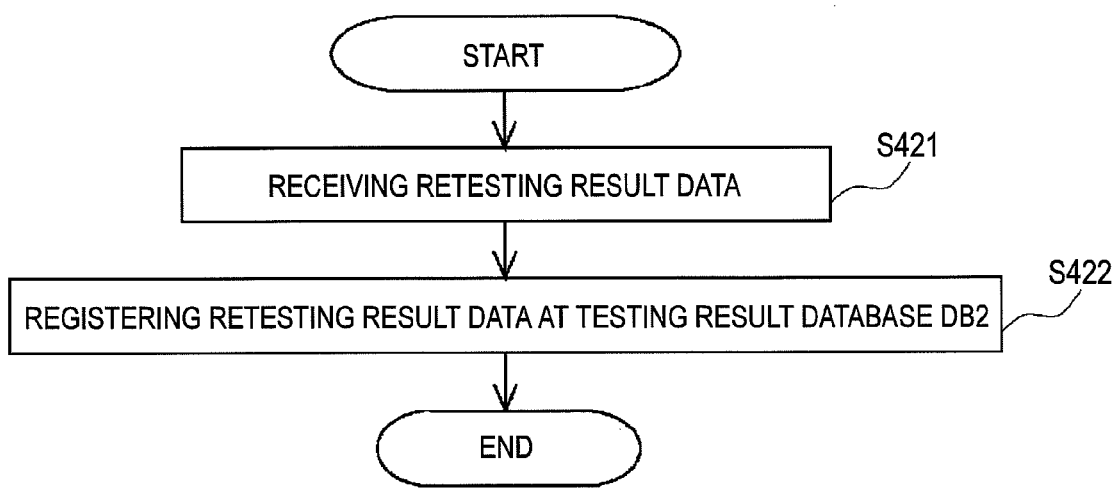
FIG. 20 is a flowchart illustrating the flow of a retesting result receiving process carried out by a testing information management apparatus according to an embodiment.

FIG. 20 is a flowchart illustrating the flow of the retesting result receiving process carried out by the testing information management apparatus 9. The retesting result data transmitted from the information processing unit 52 is received by the communication interface 91g of the testing information management apparatus 9 (Step S421). In the CPU 91a of the testing information management apparatus 9, the process of Step S422 is invoked when an event occurs in which the retesting result data is received.

In Step S422, the CPU 91a stores the received retesting result data in the testing result database DB2 (Step S422). Then, after the process of Step S422, the CPU 91a completes the retesting result receiving process.

<Operation of Sample Transport Apparatus 301>

The sample rack L delivered from the sample transport apparatus 3 which is positioned most downstream in the transport direction is introduced to the rack slider 303. The rack slider 303, of which details are omitted, receives an instruction from the system control apparatus 8, delivers the sample rack L to any one of the measurement line 302a and the skip line 302b of the conveyor 302. When the sample rack L is loaded on the measurement line 302a, the control section of the conveyor 302 operates the measurement line 302a and transports the sample rack L such that the sample container T of the smear slide preparing object is positioned at a supply position to supply the sample to the smear slide preparing apparatus 6. After the sample is completed to be supplied to the smear slide preparing apparatus 6, the measurement line 302a is further driven so as to transport the sample rack L to the sample accommodating apparatus 4. In addition, when the sample rack L is loaded on the skip line 302b, the control section of the conveyor 302 operates the skip line 302b and transports the sample rack L onto the skip line 302b so as to be unloaded to the sample accommodating apparatus 4.

<Operation of Sample Accommodating Apparatus 4>

The sample rack L delivered from the sample transport apparatus 301 is introduced to the sample accommodating apparatus 4. The sample accommodating apparatus 4 transports and accommodates the sample rack L on a rack placing section.

With the configuration as described above, even when the configuration of the sample testing system 1 is simplified and it takes a time longer than an expected time for the determination of the necessity for a retest, the sample requiring the retest can be automatically subjected to the retest.

In addition, there is no need to provide the sample testing apparatus for the dedicated retest at the sample testing system 1. In addition, since there is no need to provide the transport path of the sample rack for the dedicated retest, the entire configuration of the system can be simplified compared with the related art, so that the manufacturing cost of the system can be reduced.

In addition, since both the first-round test and the retest are measured by only one measuring unit 51 of the sample testing apparatus 5, work efficiency of the measuring unit 51 is high and, as a result, the efficiency of the whole system is high.

In addition, the necessity for the retest and the retest items are automatically determined based on the first-round testing result, and the retest for the determined retest items is automatically performed. Therefore, the system can be very easy to operate by an operator.

Furthermore, until it is determined whether or not the retest is necessary for all the samples held on the sample rack L, the transport control of the sample rack L is carried out not to proceed ahead of the after-analysis rack delivery position 391. Therefore, in a case where the sample rack L is configured to be transported in both directions X1 and X2 in the rack transport section 35 in which the sample supply position 35b and the after-analysis rack deliver position 391 exist, merely by configuring the sample rack L to be transported in only one direction in the before-analysis rack holding section 33 and the second transport mechanism 32, the sample which is determined as necessary for the retest after the first-round test is carried out can return up to the sample supply position 35b. Therefore, it is possible to reduce a portion of the sample rack L which is transported in both directions in the entire transport path of the sample rack L. As a result, the complexity in structure and the increase in size, and the steep rise in manufacturing cost can be suppressed.

(Other Embodiments)

In the above-mentioned embodiment, the configuration has been described such that the first transport mechanism 31 is controlled by the information processing unit 52 of the sample testing apparatus 5, and the second transport mechanism 32 is controlled by the control section 300 of the sample transport apparatus 3, but the invention is not limited thereto. The control of the first transport mechanism 31 and the second transport mechanism 32 may be carried out by any one of the information processing unit 52 and the control section 300. In addition, the control sections of the first transport mechanism 31 and the second transport mechanism 32 may be separately provided from the information processing unit 52 and the control section 300.

In the above-mentioned embodiment, the configuration has been described such that the transport path of the sample rack L is bent in a rectangular shape and the after-analysis rack delivery position 391 is provided at one corner of the rectangular shape, but the invention is not limited thereto. The transportation of the sample rack L may be configured such that the transport path of the sample rack L is configured to be in a linear shape and the after-analysis rack delivery position is provided in the middle (on the downstream side of the transport direction from the sample aspiration position) thereof, and the sample rack L does not move to exceed the after-analysis rack deliver position so as not to be advanced on the downstream side of the transport direction until it is determined whether or not the retest is required for all the samples held on the sample rack L.

In the above-mentioned embodiment, the configuration has been described such that the CPU executes the computer program for controlling the first transport mechanism so as to control the first transport mechanism, but the invention is not limited thereto. The control process of the first transport mechanism may be configured to be performed by dedicated hardware such as a FPGA or an ASIC which performs the same process as the controlling program of the first transport mechanism. Similarly, the control process of the second transport mechanism may be configured to be performed by dedicated hardware such as a FPGA or an ASIC which performs the same process as the controlling program of the second transport mechanism.

In the above-described embodiment, the configuration has been described in which the single computer 52a executes all the processes of the computer program 524a. However, the invention is not limited to this. A distribution system may be employed for distributing the same process as the above-described computer program 524a to plural devices (computers) and performing the process.

In the above-mentioned embodiment, the configuration has been described such that the control of the first transport mechanism 31 and the second transport mechanism 32, the determination of the necessity for the retest, and the determination of the retest items are dispersedly carried out by the information processing unit 52, the control section 300, and the testing information management apparatus 9, but the invention is not limited thereto. For example, these processes may be carried out by the information processing unit 52.

In the above-mentioned embodiment, the configuration has been described such that the sample testing apparatus 5 is the multiple blood cell analyzing apparatus, but the invention is not limited thereto. The sample testing apparatus 5 may be a urine analysis apparatus for analyzing urine or an analysis apparatus for analyzing a bone marrow fluid as long as it is an apparatus for analyzing the sample which is gathered from a human subject.

In the above-mentioned embodiment, the configuration has been described such that the sample rack L holding the sample for which the determination of the necessity for the retest is not completed is kept waiting at the after-analysis rack delivery position 391 until the necessity for the retest on the sample is determined, so that the sample for which the determination of the necessity for the retest is not completed is transported on the downstream side in the transport direction so as not to exceed the after-analysis rack delivery position 391, but the invention is not limited thereto. It may be configured such that a transport speed of the sample rack L from the sample supply position 35b up to the after-analysis rack delivery position 391 is slower than a transport speed of the sample rack L from the sending position 35a up to the after-analysis rack delivery position 391, so that the sample for which the determination of the necessity for the retest is not completed is transported on the downstream side in the transport direction so as not to exceed the after-analysis rack delivery position 391.

In the above-mentioned embodiment, the configuration has been described such that the sample which is determined as needing the retest is transported to the sample supply position 35b using the same transport path as that of the sample advancing to the after-analysis rack delivery position 391 from the sample supply position 35b, but the invention is not limited thereto. For example, the transport path for transporting the sample to be subjected to the retest to the sample supply position 35b may be provided separately from the transport path of the sample advancing to the after-analysis rack delivery position 391 from the sample supply position 35b.

In the above-mentioned embodiment, the configuration has been described such that, in a case where the sample for which the necessity for the retest is not determined when the sample reaches the after-analysis rack delivery position 391, the sample is kept waiting at the after-analysis rack delivery position 391 until the necessity for the retest is determined, but the invention is not limited thereto. For example, it may be configured such that the sample on the after-analysis rack delivery holding section 34 can be transported in both directions Y1 and Y2 so that the sample for which the necessity for the retest is not determined is kept waiting on the transport path of the after-analysis rack holding section 34.

In the above-mentioned embodiment, the configuration has been described such that when a predetermined period of time lapses from the point of starting the timer after the sample rack L is stopped at the after-analysis rack delivery position 391 and then a timer starts, a time-out occurs and the sample rack L is delivered to the after-analysis rack holding section 34, but the invention is not limited thereto. For example, the timer may start after the first-round testing results of all the samples held on the sample rack L are completely obtained. Alternatively, the timer may start after the first-round testing result of the sample which is firstly subjected to the first-round test among the plural samples held on the sample rack L is obtained. Further, the timer may start from the point of time when all the samples held on the sample rack L are taken into the measuring unit for the first-round test. Alternatively, the timer may start from the point of time when one sample is firstly taken into the measuring unit for the first-round test among the plural samples held on the sample rack L.

In the above-mentioned embodiment, the configuration has been described such that the testing information management apparatus 9 determines the necessity for the retest on the sample; the testing information management apparatus 9 transmits the necessity-for-retest determination notification data to the information processing unit 5; the information processing unit 5 sets the retest flag to "1" or "0" corresponding to each sample of the transport management table TT based on the necessity-for-retest determination notification data; by determining whether or not there is a sample of which the retest flag is set to "1" in the transport management table TT, the information processing unit 5 determines whether or not the retest on the sample held on the sample rack L is necessary; and, when there is a sample of which the retest flag is set to "1", the sample rack L is transported until the sample reaches the sample supply position 35b in order to perform the retest on the sample, but the invention is not limited thereto. It may be configured such that the necessity for the retest on the sample is determined on the outside of the sample testing system; the sample testing system obtains the necessity-for-retest determination result information indicating a determination result as to whether the necessity for the retest is necessary or not; and the sample testing system determines whether or not the retest on the sample is necessary using the necessity-for-retest determination result information. For example, it may be configured such that the necessity for the retest on the sample is determined on the outside of the sample testing system; the information processing unit 5 obtains the necessity-for-retest determination result information by manually input of an operator or by being transmitted from the outside of the system; the information processing unit 5 refers to the necessity-for-retest determination result information and sets the retest flag corresponding to each sample of the transport management table TT to "1" or "0" based on the necessity-for-retest determination result information; by determining whether or not there is a sample of which the retest flag is set to "1" in the transport management table TT, the information processing unit 5 determines the necessity for the retest on the sample held on the sample rack L; and when there is the sample of which the retest flag is set to "1", the sample rack L is transported until the sample reaches the sample supply position 35b in order to perform the retest on the sample.

What is claimed is:

1. A sample testing apparatus comprising:
a plurality of testing units, each of the plurality of testing units being for aspirating the sample from the sample container, and for performing a test on the aspirated sample;
a plurality of transport units corresponding to the plurality of testing units, each of the plurality of transport units having:
a feeding section for feeding a sample container to a first position;
a transport mechanism for transporting the sample container on a path in a first transport direction from the first position to a third position through a second position to serve the sample container to the testing unit,
wherein the transport mechanism is also configured to be capable of transporting the sample container on said path in a second transport direction opposite to the first transport direction;
a receiving section for receiving the sample container from the third position; and
a transport line for transporting the sample container to another transporting unit, and which is connected to the feeding section and the receiving section,
a determination result obtainer for obtaining one of a first determination result indicating that a second test is required for the sample and a second determination result indicating that the second test is not required for the sample, based on a test result of a first test on the sample; and
a transport controller for controlling the transport unit so as to transport the sample container positioned between the second position and the third position back to the second position on said path in the second transport direction, the sample container containing the sample on which the first test has been performed, if the determination result obtainer has obtained the first determination result on the sample,
wherein the sample container is not transported beyond the third position from the second position side before the determination result obtainer has obtained any one of the first and the second determination result on the sample.

2. The sample testing apparatus according to claim 1, wherein the transport controller controls the transport unit so as to keep the sample container waiting at the third position until the determination result obtainer has obtained any one of the first and the second determination result on the sample, if the determination result obtainer has not obtained any one of the first and the second determination result on the sample when the sample container has reached the third position.

3. The sample testing apparatus according to claim 2, wherein the transport controller controls the transport unit so as to transport the sample container beyond the third position from the second position side without keeping the sample container waiting at the third position, if the determination result obtainer has obtained the second determination result on the sample.

4. The sample testing apparatus according to claim 1, wherein the transport controller controls the transport unit so as to transport the sample container back to the second position without transporting the sample container to the third position, if the determination result obtainer has obtained the first determination result on the sample before the sample container has reached the third position.

5. The sample testing apparatus according to claim 1, wherein the transport unit is configured to transport the sample rack which holds a plurality of sample containers, each containing a sample; and
wherein the sample rack is not transported beyond the third position from the second position side before the determination result obtainer has obtained any one of the first and the second determination result on all of the samples held on the sample rack.

6. The sample testing apparatus according to claim 5, wherein the transport controller controls the transport unit so as to transport one sample container held on the sample rack back to the second position, the one sample container containing a sample on which the first test has been performed, if the determination result obtainer has obtained the first determination result on the sample in the one sample container when the determination result obtainer has not obtained any one of the first and the second determination result on a sample in another sample container held on the sample rack, the another sample container containing a sample on which the first test has been performed.

7. The sample testing apparatus according to claim 5, wherein the transport controller controls the transport unit so as to transport one sample container held on the sample rack back to the second position, the one sample container containing a sample on which the first test has been performed, if the determination result obtainer has obtained the first determination result on the sample in the one sample container when the testing unit has not performed the first test on a sample in another container held on the sample rack.

8. The sample testing apparatus according to claim 1, wherein the transport controller controls the transport unit so as to transport the sample container beyond the third position from the second position side, if the determination result obtainer has not obtained any one of the first and the second determination result on the sample within a predetermined time period.

9. The sample testing apparatus according to claim 1, wherein the transport mechanism is configured to transport the sample container along a transport path including the first position, the second position and the third position; and
wherein the transport controller controls the transport unit so as to transport the sample container back to the second position along the transport path, if the determination result obtainer has obtained the first determination result on the sample.

10. The sample testing apparatus according to claim 1, wherein the feeding section is configured to transport the sample container only in a direction toward the transport path; and
wherein the receiving section is configured to transport the sample container only in a direction separating from the transport path.

11. The sample testing apparatus according to claim 1, wherein the third position is an end position of the transport path with respect to the first transport direction; and
wherein the transport mechanism comprises a delivery mechanism for delivering the sample container located at the end position to the receiving section, and is configured to transport the sample container beyond the third position from the second position side by delivering the sample container located at the end position to the receiving section by the delivery mechanism.

12. The sample testing apparatus according to claim 1, further comprising:
a second transport unit for receiving and transporting the sample container which is transported from the transport unit; and
a sample processing unit for performing a predetermined process on the sample in the sample container transported by the second transport unit.

13. The sample testing apparatus according to claim 12, wherein the testing unit is configured to detect a blood cell in a blood, and
wherein the sample processing unit is configured to prepare a blood smear by smearing a blood on a slide glass.

14. The sample testing apparatus according to claim 1, wherein
the testing unit is configured to remove the sample container at the second position from the transport mechanism, to aspirate the sample contained in the removed sample container and to return the removed sample container to the transport mechanism.

15. A sample testing apparatus comprising:
a plurality of testing units for aspirating a sample from a sample container and performing a test on the aspirated sample;
a plurality of transport units corresponding to the plurality of testing units, each of the plurality of transport units having:
a feeding section for feeding a sample container to a first position;
a transport mechanism for transporting the sample container on a path in a first transport direction from the first position to a third position through a second position to serve the sample container to the testing unit,
wherein the transport mechanism is also configured to be capable of transporting the sample container on said path in a second transport direction opposite to the first transport direction;
a receiving section for receiving the sample container from the third position; and
a transport line for transporting the sample container to another transporting unit, and which is connected to the feeding section and the receiving section,
a determination result obtainer for obtaining one of a first determination result indicating that a second test is required for the sample and a second determination result indicating that the second test is not required for the sample, based on a test result of a first test on the sample; and
a transport controller for controlling the transport unit so as to keep the sample container waiting at the third position, the sample container containing the sample on which the first test has been performed, until the determination result obtainer has obtained any one of the first and the second determination result on the sample, if the determination result obtainer has not obtained any one of the first and the second determination result on the sample when the sample container has reached the second position, and for controlling the transport unit so as to transport the sample container back to the second position on said path in the second direction if the determination result obtainer has obtained the first determination result on the sample.

16. The sample testing apparatus according to claim 15, wherein the transport controller controls the transport unit so as to transport the sample container beyond the third position from the second position side in the first direction without keeping the sample container waiting at the third position, if the determination result obtainer has obtained the second determination result on the sample.

17. The sample testing apparatus according to claim 15, wherein the transport controller controls the transport unit so as to transport the sample container back to the second position in the second direction without transporting the sample container to the third position, if the determination result obtainer has obtained the first determination result on the sample before the sample container has reached the third position.

18. The sample testing apparatus according to claim 15, wherein
the testing unit is configured to remove the sample container at the second position from the transport mechanism, to aspirate the sample contained in the removed sample container and to return the removed sample container to the transport mechanism.

\* \* \* \* \*